US007173018B2

(12) United States Patent
Kozak et al.

(10) Patent No.: US 7,173,018 B2
(45) Date of Patent: Feb. 6, 2007

(54) PHOSPHOLIPID DERIVATIVES OF NON-STEROIDAL ANTI-INFLAMMATORY DRUGS

(75) Inventors: Alexander Kozak, Rehovot (IL); Israel Shapiro, Ramla (IL)

(73) Assignee: D-Pharm, Ltd., Rehovot (IL)

( * ) Notice: Subject to any disclaimer, the term of this patent is extended or adjusted under 35 U.S.C. 154(b) by 241 days.

(21) Appl. No.: 10/757,098

(22) Filed: Jan. 14, 2004

(65) Prior Publication Data

US 2004/0147485 A1 Jul. 29, 2004

Related U.S. Application Data

(62) Division of application No. 09/856,009, filed as application No. PCT/IL99/00623 on Nov. 18, 1999, now Pat. No. 6,730,696.

(30) Foreign Application Priority Data

Nov. 18, 1998 (IL) ..................................... 127143

(51) Int. Cl.
*A61K 31/66* (2006.01)
*C07F 9/28* (2006.01)

(52) U.S. Cl. ........................ 514/75; 514/420; 558/109; 558/70; 554/79

(58) Field of Classification Search ................ 558/169, 558/70; 548/414; 514/75, 420; 554/79
See application file for complete search history.

(56) References Cited

U.S. PATENT DOCUMENTS

| | | | | |
|---|---|---|---|---|
| 5,149,794 | A | 9/1992 | Yatvin et al. | |
| 5,256,641 | A | 10/1993 | Yatvin et al. | |
| 5,534,499 | A | 7/1996 | Ansell | |
| 5,543,389 | A | 8/1996 | Yatvin et al. | |
| 5,563,257 | A * | 10/1996 | Zilch et al. | 536/26.14 |
| 6,730,696 | B1 * | 5/2004 | Kozak et al. | 514/420 |

FOREIGN PATENT DOCUMENTS

| | | |
|---|---|---|
| JP | 11-116563 | 4/1999 |
| WO | WO 90/00555 | 1/1990 |
| WO | WO 91/16920 | 11/1991 |
| WO | WO 93/00910 | 1/1993 |
| WO | WO 96/22780 | 8/1996 |

* cited by examiner

*Primary Examiner*—Joseph K. McKane
*Assistant Examiner*—Robert Shiao
(74) *Attorney, Agent, or Firm*—Davidson, Davidson & Kappel, LLC

(57) ABSTRACT

Disclosed are compounds having non-steroidal anti-inflammatory drugs (NSAIDS) covalently linked to a phospholipid moiety via a bridging group. Also disclosed are a process for the synthesis of the compounds, pharmaceutical compositions comprising the compounds and the use thereof for the treatment of diseases and disorders related to inflammatory conditions, such as the treatment of ischemia.

30 Claims, 4 Drawing Sheets

PHOSPHOLIPID DERIVATIVES OF NON-STEROIDAL ANTI-INFLAMMATORY DRUGS

This application is a divisional of U.S. patent application Ser. No. 09/856,009 filed May 16, 2001 now U.S. Pat. No. 6,730,696 filed Nov. 18, 1999 as International Patent Application No. PCT/IL99/00623.

FIELD OF THE INVENTION

The present invention relates to compounds comprising non-steroidal anti-inflammatory drugs (NSAIDs) covalently linked to a phospholipid moiety via a bridging group, to pharmaceutical compositions comprising such compounds and to the use thereof for the treatment of diseases and disorders related to inflammatory conditions. The invention further relates to a process for the synthesis of said phospholipid derivatives of NSAIDs.

BACKGROUND OF THE INVENTION

Inflammation is an important aspect of the natural defense process. Inflammation becomes a pathological process, requiring medical intervention, when inflammatory mediators cause excessive damage to the surrounding tissue. Examples of such pathological processes are rheumatoid arthritis (RA) and psoriasis. Recently, a significant inflammatory component has been found in other types of disease, for example, neurological disorders such as multiple sclerosis and Alzheimer's disease. A common feature of many inflammatory diseases is an elevation in phospholipase $A_2$ ($PLA_2$) activity.

$PLA_2$ is the common name for a diverse group of enzymes that specifically hydrolyze the sn-2 bond of glycerophospholipid to release free fatty acids and lysophospholipids. $PLA_2$ is thought to be rate limiting in the release of arachidonic acid. The other product of its reaction, lysophospholipid, is thought to be the precursor of platelet activating factor (PAF). PAF and the arachidonic acid metabolites, eicosanoids, are pro-inflammatory lipid intermediates derived from mobilized cell membrane phospholipids by the action of phospholipase enzymes. $PLA_2$ is thus implicated as having a crucial role in the production of the entire cascade of phospholipid-derived inflammatory mediators.

For persistent inflammation three classes of drugs are widely used, corticosteroids, non-steroidal anti-inflammatory drugs (NSAIDs) and slow acting disease modifying drugs.

Corticosteroids are the most potent and effective agents in controlling inflammatory conditions. Unfortunately, prolonged use of these drugs is associated with side effects. Topical corticosteroid preparations are widely used for inflammatory dermatological conditions and inhaled corticosteroids account for 55% of the asthma market in the United Kingdom. Prednisolone is the most commonly administered corticosteroid in RA, which though possibly affecting the underlying disease process does not provide a cure and is associated with severe side-effects.

NSAIDs relieve the symptoms of inflammation without altering the course of the disease, but they have adverse gastrointestinal and renal side effects. Their main action is inhibition of arachidonate cyclooxygenase (in inflammatory cells the $COX_2$ isoenzyme) and thus inhibiting prostaglandin and thromboxane production.

Disease-modifying anti-rheumatic drugs (DMARDs) such as gold products, auranofin (SKB), chloroquine (Sanofi), sulfasalazine (Pharmacia & Upjohn), cyclosporin (Sandoz (Novartis)) and methotrexate (MTX, APH, Pharmacia & Upjohn) are second-line agents for treatment of RA. In most cases their mode of action is ill defined and the term 'slow-acting' is applied because these agents may take weeks or months to have demonstrable effect. Treatment with DMARDs has to be continued for years. If complete remission is achieved for at least six months, the dosage is gradually reduced and may be stopped altogether. DMARDs appear to decrease radiographic joint damage and improve acute-phase markers in RA but they all have adverse effects.

Diclofenac ([o-[(2,6-dichlorophenyl)amino]phenyl]acetate) is a non-steroidal anti-inflammatory drug of the phenylacetic acid class. When given orally the absorption of diclofenac is rapid and complete. It binds extensively to plasma albumin. Substantial concentrations of drug are attained in synovial fluid, which is the proposed site of action of the NSAIDs. Diclofenac is a potent inhibitor of prostaglandin synthesis and has also been shown to inhibit interleukin-1 (IL-1$\beta$) and tumor necrosis factor alpha (TNF-$\alpha$), involved in osteoarthritis. Gastrointestinal complications such as ulceration and intolerance are the most common adverse effect of diclofenac. Renal dysfunction and hypersensitivity reactions also occur. Many patients with rheumatic disorders have some degree of renal function impairment and are especially susceptible to the induction of renal failure by NSAIDs.

Other non-steroidal anti-inflammatory drugs such as salicylates, indomethacin and ibuprofen directly inhibit cyclooxygenase, a key enzyme in the synthesis pathway of prostaglandins. However, since these drugs inhibit early reactions in the arachidonic acid metabolism, they may block the formation of more than one product, hence leading to severe side effects. Indomethacin, for example, may also disrupt calcium flux across membranes, inhibit cAMP-dependent protein kinase and phosphodiesterase.

It would, therefore, be desirable to be able to extend the usefulness of NSAIDs to conditions that do not respond to lower doses of the drugs and to reduce undesirable side effects by their targeting to the diseased cells.

The use of prodrugs to impart desired characteristics such as increased bioavailability or increased site-specificity for known drugs is a recognized concept in the state of the art of pharmaceutical development. The use of various lipids in the preparation of particular types of prodrugs is also known in the background art. However, none of the background art discloses prodrugs comprising NSAIDs that upon activation by intracellular lipases enable preferential accumulation and release of the drug within the diseased cells.

International Patent Application WO 91/16920 discloses phospholipid prodrugs of salicylates and nonsteroidal anti-inflammatory drugs wherein the drug is directly linked, without any spacer, to either or both of the glycerol hydroxyls of a phospholipid or to available hydroxyls or amines of phospholipid head groups. These prodrugs, when taken orally, protect the gastric mucosa and release the active principle in the gut via the action of pancreatic enzymes.

In other examples of phospholipid prodrugs, the formulation of the prodrugs into liposomes or other micellar structures is the feature that enables their preferential uptake, for instance by liver cells or by macrophages as in the case of the phospholipid conjugates of antiviral drugs disclosed in International Patent Applications WO 93/00910 and WO 90/00555.

International Patent Application WO 96/22780 discloses compositions comprising nonsteroidal anti-inflammatory drugs non-covalently associated with zwitterionic phospholipids. In contrast, the present invention relates to nonsteroidal anti-inflammatory drugs covalently bound to a phospholipid via a spacer group.

U.S. Pat. No. 5,149,794 discloses a method for delivering drugs selectively to intracellular organelles. The disclosed compounds comprise an antiviral or antineoplastic drug covalently bound to a lipid carrier via a spacer group which may act to modulate drug release at the target site. In contrast to the present invention, the disclosed prodrug is site specific due to the existence of the lipid carrier, and drug release from the lipid conjugate is not a requirement for the drug targeting. In addition, said U.S patent does not disclose phospholipids as the lipid carriers, nor compounds comprising nonsteroidal anti-inflammatory drugs.

U.S. Pat. No. 5,256,641 discloses methods of delivering and specifically targeting antigenically-active peptides to cells for the specific production of immunological reactivity against such peptides. In contrast, the present invention does not disclose prodrugs wherein the active ingredients are peptides, though peptides may serve as a spacer between the active drug and the phospholipid.

U.S. Pat. No. 5,543,389 discloses covalent polar lipid-drug conjugates for facilitating the entry of drugs into cells at pharmokinetically useful levels. The rationale for specific activation of the prodrug in that case, are very different from the present invention. The examples of the present invention with phospholipids were not made and with hindsight it is clear that it would be ineffective to synthesize active phospholipid prodrugs if the spacer between the lipid and the drug is less than a specific length of at least 4 carbon atoms, because of unfavorable conditions due to steric hindrance and stereochemical problems.

SUMMARY OF THE INVENTION

The present invention provides, in one aspect, compounds of the general formula I Formula I

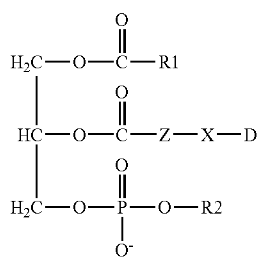

or a pharmaceutically acceptable salt thereof, wherein:

R1 is a saturated or unsaturated, substituted or unsubstituted hydrocarbon chain having from 2 to 30 carbon atoms;

R2 is H or a phospholipid head group;

D is the residue of a nonsteroidal anti-inflammatory drug having a functional group selected from the group consisting of carboxyl, hydroxyl, amine and thiol, wherein D is attached through said functional group to a bridging group, —C(O)-Z-X—, wherein Z is a saturated or unsaturated hydrocarbon chain having from 2 to 15 carbon atoms, and X is selected from amino, hydroxy, thio and carbonyl groups, such that when the functional group of D is carboxyl, X is selected from amino, hydroxy and thio, and when the functional group of D is amino, hydroxy or thio, X is a carbonyl group.

In one preferred embodiment, R1 of the above compound of formula I is a hydrocarbon chain having from 10 to 20 carbon atoms, preferably an alkyl residue of 15 or 17 carbon atoms.

According to another preferred embodiment, the nonsteroidal anti-inflammatory drug is selected from the group including, but not limited to, diclofenac, indomethacin, ibuprofen, naproxen and 6-methoxy-2-naphthylacetic acid.

In still another preferred embodiment, the phospholipid head group R2 is selected from choline, ethanolamine, inositol and serine.

Preferred according to the invention are compounds of the general formula I wherein the drug residue D is inactive while bound to the —C(O)-Z-X— bridging group and the release of the active drug is initiated by enzymatic cleavage of an ester bond at position sn-2 of the phosholipid. Preferably the enzymatic cleavage is executed by a phospholipase, more preferably phospholipase $A_2$ ($PLA_2$).

Most preferred compounds according to the invention are:

1-Stearoyl-2-{3-[2-(2,6-dichloroanilino)phenylacetamido]propanoyl}-sn-glycero-3-phosphocholine, 1-Stearoyl-2-{4-[2-(2,6-dichloroanilino)phenylacetamido]butanoyl}-sn-glycero-3-phosphatidylcholine, 1-Stearoyl-2-{5-[2-(2,6-dichloroanilino)phenylacetamido]valeroyl}-sn-glycero-3-phosphatidylcholine, 1-Stearoyl-2-{6-[2-(2,6-dichloroanilino)phenylacetamido]hexanoyl}-sn-glycero-3-phosphatidylcholine, 1-Stearoyl-2-{8-[2-(2,6-dichloroanilino)phenylacetamido]octanoyl}-sn-glycero-3-phosphatidylcholine, 1-Stearoyl-2-{12-[2-(2,6-dichloroanilino)phenylacetamido]dodecanoyl}-sn-glycero-3-phosphatidylcholine, 1-Stearoyl-2-{3-[1-(p-chlorobenzoyl)-5-methoxy-2-methyl indolylacetamido]propanoyl}-sn-glycero-3-phosphocholine, 1-Stearoyl-2-{4-[1-(p-chlorobenzoyl)-5-methoxy-2-methyl indolylacetamido]butanoyl}-sn-glycero-3-phosphocholine, 1-Stearoyl-2-{5-[1-(p-chlorobenzoyl)-5-methoxy-2-methyl indolylacetamido]valeroyl}-sn-glycero-3-phosphocholine, 1-Stearoyl-2-{6-[1-(p-chlorobenzoyl)-5-methoxy-2-methyl indolylacetamido]hexanoyl}-sn-glycero-3-phosphocholine, 1-Stearoyl-2-{8-[1-(p-chlorobenzoyl)-5-methoxy-2-methyl indolylacetamido]octanoyl}-sn-glycero-3-phosphocholine, 1-Stearoyl-2-{3-[α-methyl-4-(2-methylpropyl)benzeneacetamido]propanoyl}-sn-glycero-3-phosphocholine, 1-Stearoyl-2-{6-[α-methyl-4-(2-methylpropyl)benzeneacetamido]hexanoyl}-sn-glycero-3-phosphocholine, 1-Stearoyl-2-{3-[(S)-6-methoxy-α-methyl-2-naphtaleneacetamido]propanoyl}-sn-glycero-3-phosphocholine, 1-Stearoyl-2-{4-[(S)-6-methoxy-α-methyl-2-naphtaleneacetamido]butanoyl}-sn-glycero-3-phosphocholine, 1-Stearoyl-2-{6-[(S)-6-methoxy-α-methyl-2-naphtaleneacetamido]hexanoyl}-sn-glycero-3-phosphocholine, and 1-Stearoyl-2-{4-[2-(6-methoxynaphtyl)acetamido]butanoyl}-sn-glycero-3-phosphocholine.

Compounds of the invention are useful for the treatment of diseases and disorders related to inflammatory conditions. These compounds may serve as prodrugs that upon initial enzymatic cleavage, that may or may not be followed by further enzymatic or non-enzymatic cleavage(s), release nonsteroidal anti-inflammatory agents at the diseased site.

Thus, in another aspect, the invention provides pharmaceutical compositions comprising a pharmaceutically acceptable carrier and, as an active ingredient, a compound of the general formula I Formula I

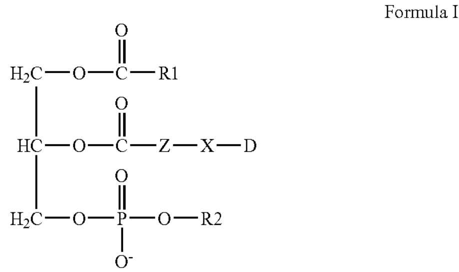

or a pharmaceutically acceptable salt thereof, wherein:

R1 is a saturated or unsaturated, substituted or unsubstituted hydrocarbon chain having from 2 to 30 carbon atoms;

R2 is H or a phospholipid head group;

D is the residue of a nonsteroidal anti-inflammatory drug having a functional group selected from the group consisting of carboxyl, hydroxyl, amine and thiol, wherein D is attached through said functional group to a bridging group, —C(O)-Z-X—, wherein Z is a saturated or unsaturated hydrocarbon chain having from 3 to 15 carbon atoms, and X is selected from amino, hydroxy, thio and carbonyl groups, such that when the functional group of D is carboxyl, X is selected from amino, hydroxy and thio, and when the functional group of D is amino, hydroxy or thio, X is a carbonyl group.

The pharmaceutical compositions of the invention are useful for the treatment of diseases and disorders related to inflammatory conditions including, but not being limited to, autoimmune diseases such as arthritis, rheumatoid arthritis, multiple sclerosis, systemic lupus erythematosus, other diseases such as asthma, psoriasis, inflammatory bowel syndrome, neurological degenerative diseases such as Alzheimer's disease, Parkinson's disease, Huntington's disease, vascular dementia, and other pathological conditions such as epilepsy, migraines, stroke and trauma.

Any suitable mode of administration of the pharmaceutical composition can be used according to the invention including, but not being limited to, oral, ocular, nasal, parenteral, topical or rectal administration. The pharmaceutical compositions may be in the form of solutions, suspensions, capsules, tablets, aerosols, gels, ointments or suppositories.

In yet another aspect, the invention provides a method for treatment of a disease or disorder related to an inflammatory condition comprising administering to a patient in need thereof a therapeutically effective amount of a compound or a pharmaceutical composition in accordance with the invention.

In still another aspect, the present invention provides a process for the synthesis of compounds in accordance with the invention. Said synthesis process comprising:

(i) providing a molecule y-X-Z-COOH, wherein y is selected from H and OH, Z is a saturated or unsaturated hydrocarbon chain having from 2 to 15 carbon atoms, and X is selected from amino, hydroxy, thio and carbonyl groups;

(ii) replacing y with an appropriate blocking group, B;

(iii) preparing an anhydride of the molecule B-X-Z-COOH;

(iv) acylating a lyso-lecithin by the anhydride of step (iii) to yield 1-acyl-2-acyl(X-B)-sn-glycero-3 phospholipid;

(v) removing the blocking group B from the functional group X; and (vi) coupling a nonsteroidal anti-inflammatory drug D to the functional group X, thus, generating a molecule of the general Formula I.

Further objects of the present invention will become apparent to those skilled in the art upon further review of the following disclosure, including the detailed descriptions of specific embodiments of the invention.

BRIEF DESCRIPTION OF THE DRAWINGS

The invention will be understood and appreciated more fully from the detailed description below, in conjunction with the drawings, in which.

DETAILED DESCRIPTION OF THE INVENTION

Figure 1:
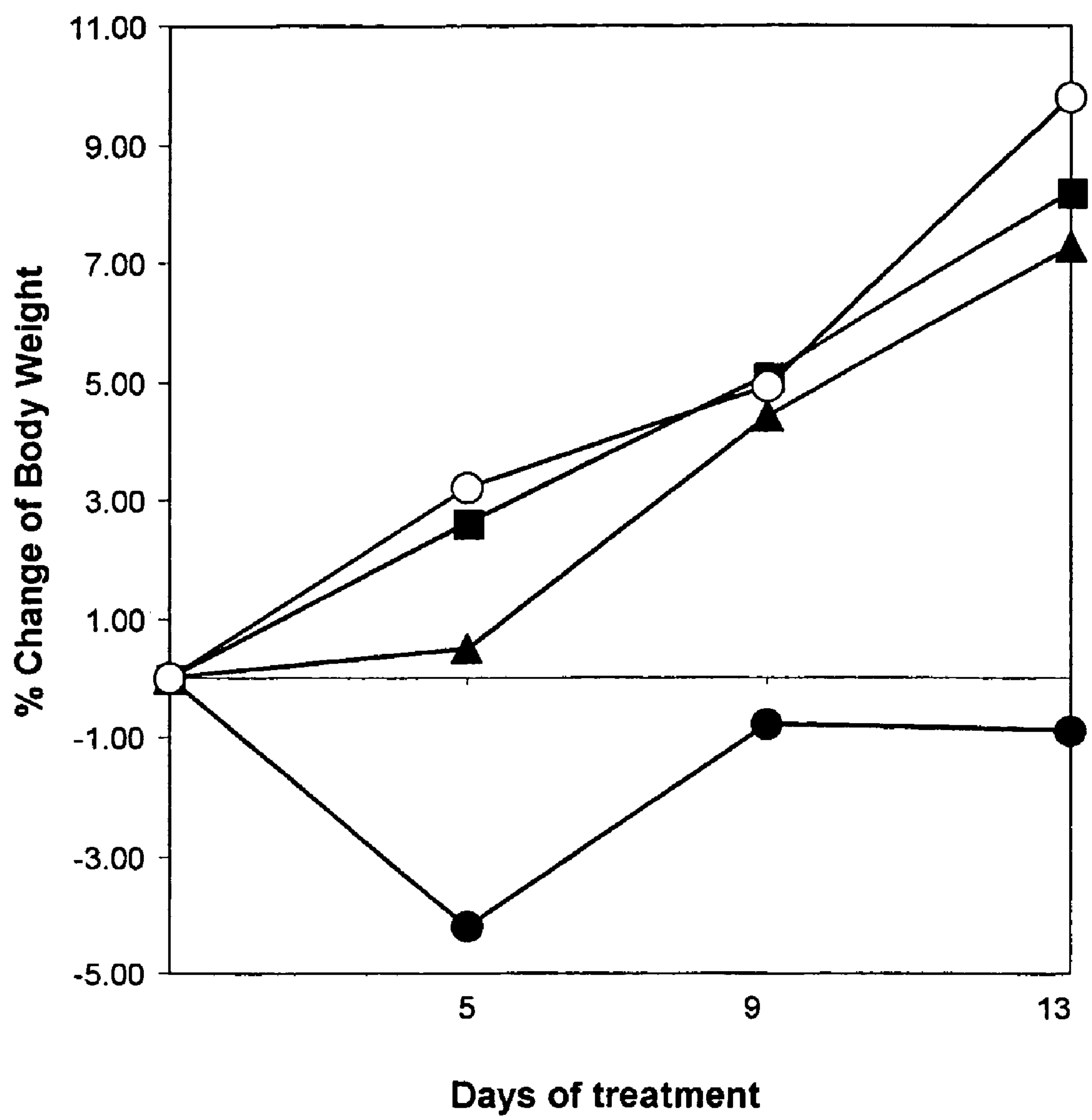
FIG. 1 depicts body weight changes (%) of rats treated with multiple per os gavage of either vehicle (open circles), 10 mg/kg diclofenac (DCF, filled circles), 30 mg/kg 1-Stearoyl-2-{4-[2-(2,6-dichloroanilino)phenylacetamido] butanoyl}-sn-glycero-3-phosphocholine (denoted DP-DCF; Z=3; filled squares) or 30 mg/kg 1-Stearoyl-2-{6-[2-(2,6-dichloroanilino)phenylacetamido]hexanoyl}-sn-glycero-3-phosphocholine (denoted DP-DCF; Z=5; filled triangles).

The present invention relates to a group of novel compounds comprising nonsteroidal anti-inflammatory drugs (NSAIDs) covalently conjugated, via a bridging group, to position sn-2 of a phospholipid.

The compounds according to the invention are phospholipid derivatives wherein the conjugated NSAID residue is pharmacologically inactive, and regulated release of the active drug occurs at the site of a diseased tissue. The compounds, being hydrophobic in nature, may penetrate biological membranes and barriers, thus effectively transporting the attached prodrug into cells or organs. The specificity of the activation of the anti-inflammatory prodrug is afforded by the bridging group that is designed to be sensitive to cleavage by phospholipases (e.g. $PLA_2$) that are specifically elevated at the disease site. Hence, accumulation of the active drug occurs at the site of the disease, whereas, in healthy tissue there will be only a basal level of prodrug cleavage.

It should be appreciated that the novel compounds of the invention wherein the NSAIDs are introduced as prodrugs, are more effective than their corresponding free drugs in at least two aspects: (i) having increased therapeutic efficacy at relatively lower doses, and (ii) exhibiting reduced side effects and toxicity.

Accordingly, it is possible to extend the usefulness of NSAIDs to conditions that do not respond to lower doses of the drug and to reduce undesirable side effects by the regulated release of the active drug at the diseased site. According to a preferred embodiment, the released drug is identical to the corresponding original drug used for the synthesis of a compound of the invention, hence it is expected to have a similar breadth of therapeutic activity. Also useful are drug derivatives that although released from the phospholipid molecule, remain conjugated to the whole or part of the bridging group, while still capable of exerting therapeutic effects comparable to those of the original drug D.

The compounds of the invention are of the general formula I

Formula I

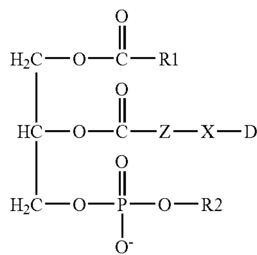

or a pharmaceutically acceptable salt thereof, wherein:

R1 is a saturated or unsaturated, substituted or unsubstituted hydrocarbon chain having from 2 to 30 carbon atoms;

R2 is H or a phospholipid head group;

D is the residue of a nonsteroidal anti-inflammatory drug having a functional group selected from the group consisting of carboxyl, hydroxyl, amine and thiol, wherein D is attached through said functional group to a bridging group, —C(O)-Z-X—, wherein Z is a saturated or unsaturated hydrocarbon chain having from 2 to 15 carbon atoms, and X is selected from amino, hydroxy, thio and carbonyl groups, such that when the functional group of D is carboxyl, X is selected from amino hydroxy and thio, and when the functional group of D is amino, hydroxy or thio, X is a carbonyl group.

It is desired that the generated covalent bond between the bridging group and the drug derivative, i.e. the X-D bond, is a stable ester-, amide- or thioester bond that does not dissociate spontaneously under physiological conditions.

In designing a compound according to the invention, to be used as a prodrug, the specific nature of the inflammatory condition to be treated should be considered. This involves determining the desired pharmacological activity to be achieved hence the choice of the drug D, and identifying the particular site where the desired pharmacological activity is needed.

It should be noted that the number of carbon atoms in said R1 chain of a compound of the general formula I, is determined according to the desired lipophilicity of the molecule. The lipophilicity of the molecule is directly correlated to the selected hydrocarbon chain length. R1 chains according to the invention may contain 2 to 30 carbon atoms. Molecules with R1 having from 10 to 20 carbon atoms are most desired as endowing the molecule with suitable hydrophobicity for crossing biological membranes and at the same time providing adequate substrate for the action of the phospholipase.

R1 may be a saturated or unsaturated hydrocarbon chain, containing one or more double bonds. One or more hydrogen atoms on the chain may be substituted, for example, by halogen atoms or by a small alkyl group such as methyl residues, with the proviso that the substituents still allow free access for the desired cleaving enzymes.

In preferred embodiments of the invention R1 is an alkyl residue of an odd number of carbon atoms. More preferably R1 is an alkyl residue of 15 or 17 carbon atoms yielding, respectively, the naturally occurring palmitoyl ($C_{16}$) or stearoyl ($C_{18}$) residues at the $\alpha$ position of the phospholipid.

The selection of the anti-inflammatory drug residue D to be included in the compound of the general formula I is dependent on the disease or disorder intended to be treated. Any nonsteroidal anti-inflammatory drug that possesses a free —C(O)OH, —OH, —$NH_2$, —NH or —SH group available for reaction with the functional group of the bridging group to form a stable covalent bond D-X, may be selected. Suitable NSAIDs include, but not limited to, drugs presently known on the market, for instance:

1) arylacetic acid derivatives such as diclofenac, etodolac, ibufenac and indomethacin, 2) arylcarboxylic acid derivatives such as ketorolac, 3) aminoarylcarboxylic acid derivatives such as flufenamic acid, meclofenamic acid, mefenamic acid and niflumic acid, 4) arylpropionic acid derivatives such as fenoprofen, ibuprofen, ketoprofen and naproxen, 5) salicylic acid derivatives such as fendosal, mesalamine and salsalate, and 6) thiazinecarboxamides such as piroxicam and tenoxicam.

Also qualified as D are active metabolites or derivatives of NSAIDs that preserve their anti-inflammatory activity provided that they have an available functional group, as mentioned above, readily available for reacting with the appropriate bridging group. A particular example for this kind of drug is the compound 6-methoxy-2-naphthylacetic acid which is an in vivo metabolite of nabumetone [4-(6-methoxy-2-naphthyl)-butan-2-one].

Currently preferred embodiments according to the invention are selected from, but are not limited to, prodrugs wherein D is a residue of diclofenac, indomethacin, ibuprofen, naproxen and 6-methoxy-2-naphthylacetic acid. However, any presently known nonsteroidal anti-inflammatory drugs or those that will be available in the future are included within the scope and concept of the present invention provided that said drugs contain either a carboxyl, hydroxyl, primary or secondary amine or thiol group available for participating in the covalent bond with component X of the bridging group.

It is desirable to provide a compound of the general formula I wherein the anti-inflammatory drug is capable of specifically inhibiting an enzyme which plays a central role in evoking inflammatory processes leading to a disease or disorder, while having no deleterious effects on other basic processes of the cell. Such desirable drugs are, for example, Celecoxib (Searle & Co.) and Meloxicam (Boehringer, Ingelheim) which are capable of differentially inhibiting the enzyme cyclooxygenase 2 (COX 2) induced in inflammatory cells, and not cyclooxygenase 1 (COX1) which is involved in normal homeostasis.

The choice of the preferred bridging group, —C(O)-Z-X—, is dependent on several considerations; it should participate in a stable covalent bond with the D moiety while lending itself to cleavage at the target site. A preferred bridging group is such that is resistant to cleavage under normal physiological conditions encountered by the administered compound on its way to the target site. The bridging group should not confer a steric hindrance on the enzymatic cleavage of the ester bond at position sn-2 of the phospholipid of the general formula I.

Depending on the treated inflammatory condition and the particular diseased cell or organs, it will be desirable at times to choose such a bridging group that will regulate the release of the active drug by facilitating or delaying its cleavage from the prodrug molecule.

According to a preferred embodiment, the total number of carbon atoms in the bridging group C(O)-Z-X is at least 6 but at most 15. It was found that this length of carbon chain provides a spacer which enables good access to an enzyme, preferably phospholipase and in particular $PLA_2$, for digesting the ester bond at position sn-2 of the phospholipid of the general formula I. Shorter spacers, in particular bridging groups comprising less than four carbon atoms, may be problematic, by creating an unfavorable steric environment for the action of the phospholipase. A situation of steric interference may also be generated by long spacers, i.e. when the number of carbon atoms in the bridging chain is greater than 15.

X may be selected from amino, hydroxy, thio and carbonyl groups with the proviso that when the functional group of D is —C(O)OH, X is not a carbonyl, and when the functional group of D is —OH, —$NH_2$, —NH or —SH, X is a carbonyl group.

Some combinations of X with particular drugs may be unfavorable as yielding a very labile bond which is spontaneously cleaved, therefore greatly lowering the efficacy of the prodrug. Such an unfavorable combination is, for instance, when the functional group of D is a carboxyl group, such as, for example, in diclofenac, forming a covalent bond with X which is a carbonyl group. The resulted bond —(CO)—O—(CO)— is a labile bond that tends to dissociate.

The therapeutic efficacy of any particular compound according to the invention should be evaluated by a person skilled in the art considering the general knowledge in pharmacology and the teachings of the present invention. The choice of a specific compound to be used as a prodrug according to the invention will also depend on the particular disease or disorder to be treated.

It is suggested that the release of the active drug at the target site is initiated by a first cleavage of the compound at position sn-2 of the phospholipid, preferably by a phospholipase, more preferably phospholipase $A_2$. $PLA_2$ is the more preferred cleaving enzyme for two compelling reasons; (i) its enhanced activity is a common feature in many inflammatory processes and (ii) it is abnormally elevated during the progression of the inflammatory disease. Thus, the drug linked to the lipid will preferentially be released at the site of the inflammation due to the increased $PLA_2$ activity. In accordance with the invention, the phospholipid-NSAID conjugate prodrug is designed to have several distinct advantages over the parent drug, including improved efficacy, potency and pharmacokinetic properties, together with reduced toxicity. It is expected that with the aforementioned advantages, the prodrug compounds of the invention will be efficient alternative novel drugs for inflammatory-related diseases and disorders.

The first cleavage at position sn-2 of the phospholipid, may further facilitate the following cleavage necessary for releasing the active NSAID from the bridging group. This second cleavage may be enzymatically or non-enzymatically executed. Candidate enzymes for performing the second cleavage may include an amidase, esterase or any other suitable enzyme functionally available at the diseased site.

Alternatively, the release of an active anti-inflammatory drug from the D-X bond may be initiated by any cleavage at position sn-2 of the phospholipid that leads to release of an active drug. Moreover, under some circumstances the active drug released may be different from the original parent drug molecule. This includes drug derivatives wherein a chemical group(s) has been removed from or added to the D structure. These cases are also included within the concept of the invention provided that the resulted drug derivative preserves its therapeutic capability. Preferably the cleavage process of the molecule of the invention is initiated specifically at the diseased cells, thus generating a highly specific and highly effective drug released at the desired target site.

Irrespective of the exact mechanism of action, it is evident that the novel compounds of the invention have an enhanced therapeutic profile. Furthermore, they are more effective than their corresponding parent drugs in at least two aspects: (i) increased specificity, and (ii) decreased side effects. The compounds of the invention may enable extending the usefulness of NSAIDs to conditions that do not respond to lower doses of the drug as well as reducing undesirable side effects by preferential releasing of the active drug at the diseased site.

In accordance with another aspect of the invention, there are provided pharmaceutical compositions comprising, as an active ingredient, a compound of the general formula I wherein Z of the bridging group having 3 to 15 carbon atoms, and a pharmaceutically acceptable diluent or carrier as are known in the art.

The pharmaceutical compositions may be in a liquid, aerosol or solid dosage form, and may be formulated into any suitable formulation including, but not limited to, solutions, suspensions, micelles, emulsions, microemulsions, aerosols, ointments, gels, suppositories, capsules, tablets, and the like, as will be required for the appropriate route of administration.

Compounds of the invention are useful in the treatment of diseases and disorders related to an inflammatory condition. Thus, in yet another aspect, the present invention provides a method for treating such an inflammatory-related disease or disorder, comprising administering to an individual in need thereof a therapeutically effective amount of a compound of the general formula I or a pharmaceutical composition in accordance with the invention. The term "therapeutically effective amount" used in the specification refers to the amount of a given prodrug compound according to the invention which antagonizes or inhibits activities associated with inflammatory processes, hence providing either a subjective relief of a symptom(s) or an objectively identifiable improvement as noted by the clinician or other qualified observer.

In particular, the present invention provides a method for treating a disease or disorder related to inflammatory condition including, but not being limited to, autoimmune diseases such as arthritis, rheumatoid arthritis, multiple sclerosis, systemic lupus erythematosus, other diseases such as asthma, psoriasis, inflammatory bowel syndrome, neurological degenerative diseases such as Alzheimer's disease, Parkinson's disease, Huntington's disease, vascular dementia, and other pathological conditions such as epilepsy, migraines, stroke and trauma.

Any suitable route of administration is encompassed by the invention including, but not being limited to, oral, intravenous, intramuscular, subcutaneous, inhalation, intranasal, topical, rectal or other known routes. In preferred embodiments, the pharmaceutical compositions of the invention are orally or nasally administered.

The dose ranges for the administration of the compositions of the invention are those large enough to produce the desired protective effect. The dosing range of the prodrug varies with the specific drug used, the treated inflammatory condition or neurological disorder, the route of administration and the potency of the particular prodrug molecule in releasing the drug at the specific target site. The dosage administered will be dependent upon the age, sex, health, weight of the recipient, concurrent treatment, if any, frequency of treatment and the nature of the effect desired. Dosage regimen and means of administration will be determined by the attending physician or other person skilled in the art.

In still another aspect, the present invention provides a method for synthesizing compounds of the above-defined formula I by following the steps of the detailed scheme of synthesis described hereinbelow. A particular synthesis scheme is depicted in Scheme I and exemplified in Examples 1 to 5. Generally speaking the synthesis process involves the following steps:

Step 1: protection of the functional moiety X on the bridging group. The purpose of this step is to prevent chemical reactions of X during the coupling of the bridging group to the lyso-lecithin molecule, so that linking of the bridging group to the lipid is exclusively mediated through the carboxyl group of the linker HO(O)C-Z-X.

Any blocking group that reacts with the functional moiety X to mask its reactive function and is readily removable after coupling may be employed. Reagents suitable for use as protecting groups are well known to those skilled in the art and include, but are not limited to, the following: benzyl chloroformate, dibenzyl dicarbonate (for NH2 or NH protection), benzyloxymethyl chloride, dihydropyran (for OH protection), diphenylcarbinol, trimethylacetamidocarbinol (for SH protection) and methoxymethyl chloride (for COOH protection).

Appropriate blocking reagents and protocols for their usage are described in *Protecting Groups* by Kocienski, P. (Thieme foundation of organic chemistry series, 1994) and in *Protective Groups in Organic Synthesis* by Greene, T. and Wuts, P. (John Wiley & Sons, Inc. 1991), the teachings of which are incorporated herein by reference.

Step 2: Preparation of an anhydride of the protected bridging group. The formation of the anhydride is performed by employing a reagent which removes one molecule of water from two protected bridging groups. This reaction is preferably performed under inert atmosphere. A commonly used reagent for this reaction is, for example, dicyclohexylcarbodiimide (DCC).

Step 3: Coupling of the protected bridging group to a lyso-lecithin. This step is carried out by acylating the appropriate phospholipid at position sn-2 to yield 1-acyl-2-acyl(X-protected)-sn-glycero-3 phospholipid. The anhydride of the protected bridging group and the corresponding lyso-lecithin are dissolved in organic solvent, for example chloroform or methylene chloride, in the presence of a catalyst, for example a tret-amine such as dimethylaminopyridine (DMAP).

Step 4: Removal of the blocking group from the functional group X. Protocols for removal of the blocking groups used in step 1 for protecting the functional group X, are disclosed in *Protecting Groups* by Kocienski, P. (Thieme foundation of organic chemistry series, 1994) and in *Protective Groups in Organic Synthesis* by Greene, T. and Wuts, P. (John Wiley & Sons, Inc. 1991). In a particular procedure, the protecting group is removed by hydrogenation in the presence of Pd/C.

Step 5: Coupling a nonsteroidal anti-inflammatory drug to the lipid moiety. Coupling of the corresponding drug to the functional group X of the bridging group is the last stage in the protocol for the synthesis of the compounds in accordance with the invention. This reaction is conducted in an organic solvent in the presence of reagents that enable a condensation reaction where water molecules are removed. Such commonly used reagents are, for example, the combination of triphenylphosphine and aldrithiol-2.

Contrary to other known procedures for the synthesis of lipid derivatives of drugs, the present protocol is unique in designating the drug conjugation step as the final one. It is important that the drug is added at the last step in order to prevent possible modifications and deterioration to its structure. Thus the process disclosed in the present invention is advantageous in terms of higher yield of the desired reaction product and much reduced levels of side products.

In a preferred embodiment, the reacting functional groups that form the X-D bond are —C(O)OH and $NH_2$ or NH groups, yielding a peptide bond. The carboxyl or the amino groups may be provided by either group X on the bridging group, or as an available functional group on the drug molecule. According to that preferred embodiment, when the reacting group of the drug is a carboxyl, it is reacted with an amine on the bridging group, and vice versa, when the reacting group of the drug is an amine, its reacting counterpart on the bridging group is a carboxyl.

EXAMPLES

A particular scheme for the synthesis of compounds of the invention is outlined in Scheme I. This scheme is exemplified below, in Examples 1 to 5, by the detailed description of the synthesis of specific lipid derivatives of diclofenac ([o-(2,6-dichloroanilino)phenyl]acetic acid), indomethacin, (1-(p-chlorobenzoyl)-5-methoxy-2-methyl-3-indolylacetic acid), ibuprofen (2-(4-isobutylphenyl)propionic acid), naproxen (d-2-(6-methoxy-2-naphthyl)pro-pionic acid) and 6-methoxy-2-naphthylacetic acid conjugated to phosphatidylcholine. This synthesis is a six-stage process: The first stage is protection of the functional group on the linker, in this case the amino group of an amino acid. The second stage is preparation of anhydride of this protected amino acid. The third stage is the formation of lipid derivative comprising the protected amino acid and a lyso-lecithin. The removal of the protecting group to yield the amino acid lipid conjugate is carried out in the fourth and fifth stages. Linking of the corresponding drug, in these particular examples, diclofenac, indomethacin, ibuprofen, naproxen or 6-methoxy-2-naphthylacetic acid to 1-acyl-2-(n-aminoacyl)-sn-glycero-3-phosphocholine is realized in the last stage.

Scheme I

A scheme for synthesis of phosphatidylcholine derivatives of diclofenac, indomethacin, ibuprofen, naproxen, and 6-methoxy-2-naphthylacetic acid.

Step 1:

$$C_6H_5CH_2OC(O)Cl + H_2N—(CH_2)_n—COOH \longrightarrow C_6H_5CH_2OC(O)—NH—(CH_2)_n—COOH + HCl.$$

Step 2:

$$2\,C_6H_5CH_2OC(O)—NH—(CH_2)_n—COOH + c\text{-}C_6H_{11}—N{=}C{=}N—C_6H_{11}\text{-}c \longrightarrow [C_6H_5CH_2OC(O)—NH—(CH_2)_n—C(O)]_2O + (c\text{-}C_6H_{11}NH)_2CO$$

Step 3:

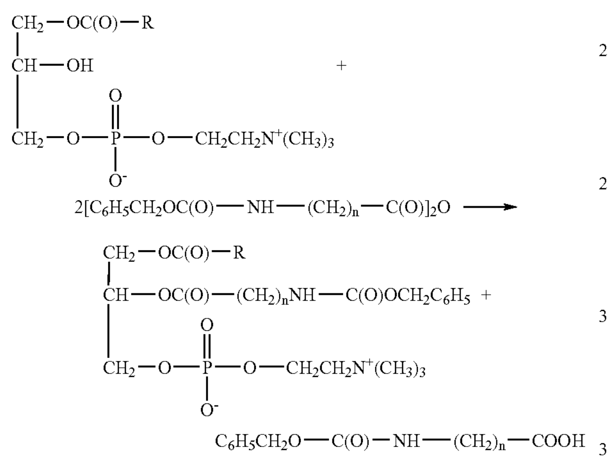

Step 4:

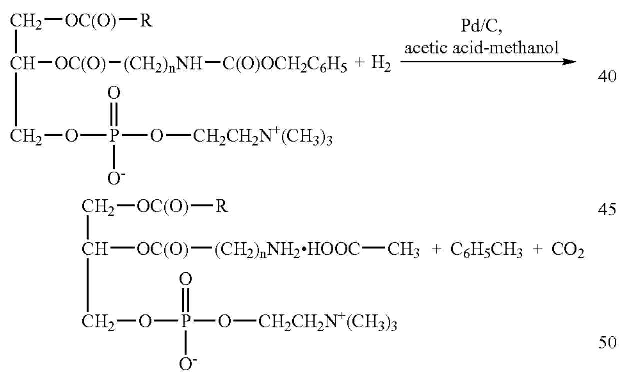

Step 5:

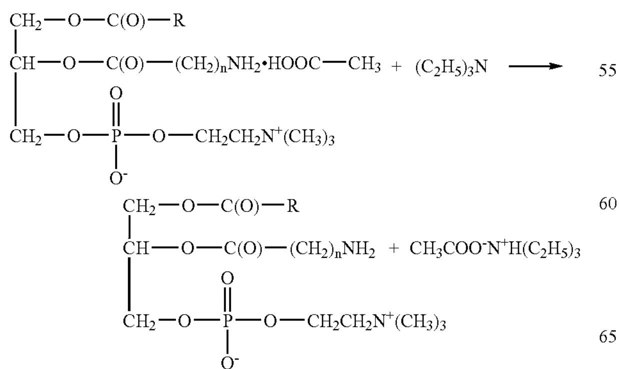

-continued

Step 6:

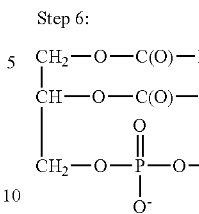

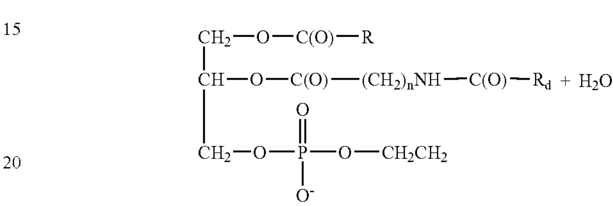

Wherein HOOC-$R_d$ in the synthesis scheme is a non-steroidal anti-inflammatory drug. For example, HOOC-$R_d$ may be selected from:

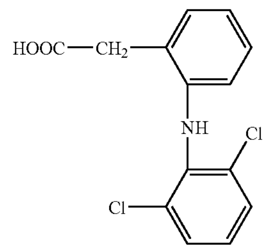

Diclofenac

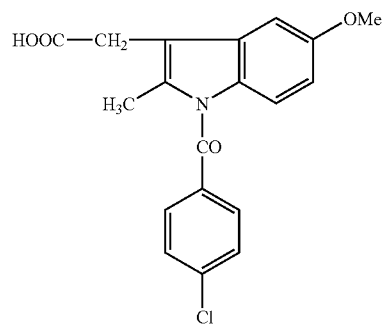

Indomethacin

HOOC—CH—CH₃ (4-isobutylphenyl)

Ibuprofen

-continued

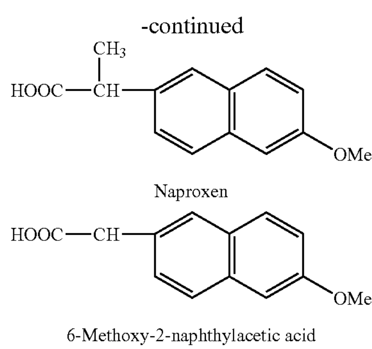

Naproxen

6-Methoxy-2-naphthylacetic acid

Example 1

Preparation of Lipid Derivatives of Diclofenac (DP-DFC)

Stage 1. Protection of the Amino Group of Amino Acid (Preparation of Z-Amino Acid).

To a mixture of 0.1 mol corresponding amino acid (aminopropanoic acid, aminobutanoic acid, aminovaleric acid, aminohexanoic acid or aminooctanoic acid) in ethanol (25 ml) in round-bottom flask (250 ml) equipped with a magnetic stirrer and dropped funnel, a solution of NaOH (8.8 g., 0.22 mol) in 100 ml water is added and the mixture is stirred by magnetic stirrer until fully dissolved. The obtained solution is cooled to 0° C. in an ice-water bath, and benzyl chloroformate (27.4 g, 0.15 mol) is added drop wise over 30 min. The reaction mixture is stirred for 3 hours at 0° C. Subsequently, about 100 ml water is added to the reaction solution and the mixture is poured into separated funnel. The solution is washed with diethyl ether (3×50 ml). The water fraction is separated and acidified with HCl (3N) to pH=1 while cooling in an ice-water bath. If a precipitate is formed, it is filtered, washed with water and dissolved in 100 ml chloroform. The chloroform solution is dried with sodium sulfate for two hours. Then the sodium sulfate is separated from the chloroform solution by filtration and the solvent is evaporated in evaporator under vacuum. The residue is washed with hexane, and dried overnight in vacuum over phosphorus pentoxide ($P_2O_5$).

If the precipitate is not formed, or in order to maximize the product yield, the acidified aqueous fraction is washed with chloroform (2×50 ml). The chloroform extracts are combined and washed with water (50 ml). The following operations with this solution are the same as for the above-described chloroform solution of the precipitate, namely, drying with sodium sulfate for two hours, then separating the sodium sulfate from the chloroform solution by filtration and evaporating the solvent in evaporator under vacuum. The residue is then washed with hexane, and dried overnight in vacuum over phosphorus pentoxide ($P_2O_5$).

All products were analyzed on TLC as follows:

TLC analysis. Silica gel 60 on aluminum sheet. Eluent is chloroform-methanol (4:1 v/v). Indicator is a spray of the composition: 4-methoxybenzaldehyde (10 ml), absolute ethanol (200 ml), 98% sulfuric acid (10 ml) and glacial acetic acid (2 ml). The chromatogram is sprayed with the indicator and then charred using hot air at 150–180° C.

The following are the intermediate products resulted at the end of stage 1 of the synthesis procedure:

3-(Benzyloxycarbonylamino)propanoic acid.

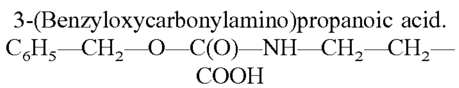
$C_6H_5$—$CH_2$—O—C(O)—NH—$CH_2$—$CH_2$—COOH

White solid. Yield 60%. TLC analysis: One spot $R_f$ 0.7. $^1$H NMR ($CD_3OD$), δ(ppm): 2.46–2.52 (t, 2H), 3.29–3.39 (t, 2H) 5.06 (s, 2H), 7.27–7.32 (m, 5H).

4-(Benzyloxycarbonylamino)butanoic acid.

$C_6H_5CH_2$—O—C(O)—NH—$(CH_2)_3$—COOH

White solid. Yield 60%. TLC analysis: One spot. $R_f$ 0.7. $^1$H NMR ($CD_3OD$), δ (ppm): 1.71–1.82 (m, 2H), 2.28–2.34 (t, 2H), 3.10–3.17 (t, 2H), 5.06 (s, 2H), 7.26–7.34 (m, 5H).

5-(Benzyloxycarbonylamino)valeric acid.

$C_6H_5CH_2$—O—C(O)—NH—$(CH_2)_4$—COOH

White solid. Yield 60%. TLC analysis: One spot. $R_f$ 0.7. $^1$H NMR ($CD_3OD$), δ (ppm): 1.45–1.50 (m, 2H), 1.56–1.62 (m, 2H), 2.25–2.31 (t, 2H), 3.08–3.13 (t, 2H), 5.05 (s, 2H), 7.26–7.34 (m, 5H).

6-(Benzyloxycarbonylamino)hexanoic acid.

$C_6H_5CH_2$—O—C(O)—NH—$(CH_2)_5$—COOH

White solid. Yield 50%. m.p. 54–56° C. TLC analysis: One spot. $R_f$ 0.7. $^1$H NMR ($CD_3OD$), δ (ppm): 1.30–1.63 (several m, 6H), 2.24–2.30 (t, 2H), 3.07–3.13 (t, 2H), 5.05 (s, 2H), 7.29–7.34 (m, 5H).

8-(Benzyloxycarbonylamino)octanoic acid.

$C_6H_5CH_2$—O—C(O)—NH—$(CH_2)_7$—COOH

White solid. Yield 50%. TLC analysis: One spot. $R_f$ 0.7. $^1$H NMR ($CD_3OD$), δ (ppm): 1.32 (broad s, 6H), 1.47–1.50 (m, 2H), 1.53–1.59 (m, 2H), 2.23–2.29 (t, 2H), 3.06–3.12 (t, 2H), 5.05 (s, 2H), 7.29–7.34 (s, 5H).

12-(Benzyloxycarbonylamino)dodecanoic acid.

$C_6H_5CH_2$—O—C(O)—NH—$(CH_2)_{11}$—COOH

White solid. Yield 50%. TLC analysis: One spot. $R_f$ 0.7. $^1$H NMR ($CD_3OD$), δ (ppm): 1.30 (broad s, 14H), 1.48–1.51 (m, 2H), 1.54–1.59 (m, 2H), 2.25–2.29 (t, 2H), 3.06–3.13 (t, 2H), 5.05 (s, 2H), 7.29–7.34 (s, 5H).

Stage 2. Synthesis of Z-Amino Acid Anhydride.

The solution of corresponding Z-amino acid produced at stage 1 (0.05 mol) in freshly distilled dichloromethane (25 ml) is introduced, under an inert atmosphere of argon, into double-neck round-bottom flask (100 ml) equipped with magnetic stirrer and dropped funnel. A solution of dicyclohexylcarbodiimide (0.0325 mol) in 25 ml of freshly distilled dichloromethane, also under argon, is added drop wise, with stirring, to the solution of Z-amino acid. After 20 min of stirring, the obtained precipitate of urea is filtered and the solution evaporated under vacuum. The crude residue is washed with hexane (2×20 ml) and then dried in vacuum.

TLC analysis: The same procedure is used for TLC analysis of the anhydrides of all Z-amino-acids. Silica gel 60 on aluminum sheet. Fluent is the mixture of chloroform with acetone (8:2, v/v). For indication, ninhydrine spray is used on the chromatogram followed by charring with hot air (100° C.).

Anhydride of 3-(Z-amino)propanoic acid.

White solid. Yield is 70%. TLC analysis: One spot $R_f$ 0.8. Chemical analysis. $C_{22}H_{24}N_2O_7$. Calculated: C, 61.68%; H, 5.60%; N, 6.54%. Found: C, 61.20%; H, 5.52%; N, 6.50%.

Anhydride of 4-(Z-amino)butanoic acid.

White solid. Yield is 70%. TLC analysis: One spot. $R_f$ 0.8. Chemical analysis. $C_{24}H_{28}N_2O_7$. Calculated: C, 63.16%; H, 6.14%; N, 6.14%. Found: C, 62.77%; H, 6.36%; N, 5.88%.

Anhydride of 5-(Z-amino)valeric acid.

White solid. Yield is 70%. TLC analysis: One spot. $R_f$ 0.8. Chemical analysis. $C_{26}H_{32}N_2O_7$. Calculated: C, 64.46%; H, 6.61%; N, 5.78%. Found: C, 64.09%; H, 6.86%; N, 5.49%.

Anhydride of 6-(Z-amino)hexanoic acid.

White solid. Yield is 70%. TLC analysis: One spot. $R_f$ 0.8. Chemical analysis: $C_{28}H_{36}N_2O_7$. Calculated: C, 64.46%; H, 6.61%; N, 5.79%. Found: C, 64.39%; H, 6.85%; N, 5.52%.

Anhydride of 8-(Z-amino)octanoic acid.

White solid. Yield is 75%. TLC analysis: One spot. $R_f$ 0.85. Chemical analysis: $C_{32}H_{44}N_2O_7$. Calculated: C, 67.60%; H, 7.75%; N, 4.93%. Found: C, 67.44%; H, 7.79%; N, 4.72%.

Anhydride of 12-(Z-amino)dodecanoic acid.

White solid. Yield is 70%. TLC analysis: One spot. $R_f$ 0.85. Chemical analysis: $C_{40}H_{60}N_2O_7$. Calculated: C 72.29%; H, 9.04%; N, 4.21%. Found: C, 72.02%; H, 9.42%; N, 4.12%.

Stage 3. Preparation of 1-acyl-2-(Z-aminoacyl)-sn-glycero-3-phosphocholine.

The anhydride of the corresponding Z-amino acid, 0.01 mol dissolved in 150 ml of freshly distilled chloroform, is introduced, under an inert atmosphere of argon, into a single-neck round-bottom flask (250 ml) equipped with a magnetic stirrer. To this solution 0.01 mol (1.22 g) 4-(dimethylamino)pyridine (DMAP) in 25 ml chloroform is added, followed by addition of a suspension of 0.0056 moles lyso-lecithin in 50 ml of chloroform. The reaction mixture is vigorously stirred for 3–5 hours at room temperature. The lyso-lecithin dissolves and reaction mixture becomes transparent after about 2 hours of stirring. The reaction is monitored by TLC using silica gel 60 on aluminum sheet, the eluent is chloroform:methanol:water, 65:35:5, the indicator is a spray of the composition: 4-methoxybenzaldehyde (10 ml), absolute ethanol (200 ml), 98% sulfuric acid (10 ml) and glacial acetic acid (2 ml). The chromatogram is sprayed with the indicator followed by charring with hot air at 150° C. The reaction is assumed to be complete and stopped when all the lyso-lecithin has disappeared. The reaction mixture is then transferred into a separating funnel and washed with a solution of 1% HCl (3×50 ml), then with saturated solution of sodium bicarbonate (3×50 ml) and finally with water (3×50 ml). The obtained product in the organic solution is dried over sodium sulfate and then filtered. The solvent is evaporated at 30° C. in a vacuum and the residue is washed with hexane and left to dry overnight under vacuum. The resulted molecule 1-acyl-2-(Z-aminoacyl)-sn-glycero-3-phosphocholine is the main product of the reaction.

The second product of the reaction is the Z-amino acid. In order to increase the yield of this product, it is back-extracted from reaction mixture as follows: The sodium bicarbonate aqueous fractions are collected and combined and then acidified by 3 N HCl to pH 1. The Z-amino acid is extracted by chloroform (2×50 ml). The chloroform extracts were combined, washed once with water and dried over sodium sulfate for 30 min with stirring. The sodium sulfate is removed by filtration, and the chloroform evaporated. Subsequently, the residue is washed with hexane and dried over $P_2O_5$ in a vacuum.

TLC analysis: Silica gel 60 on aluminum sheet. Eluent is chloroform/methanol/water (65:35:5, v/v). Indicator is a spray of the composition: 4-methoxybenzaldehyde (10 ml), absolute ethanol (200 ml), 98% sulfuric acid (10 ml) and glacial acetic acid (2 ml). The chromatogram is sprayed with the indicator and then charred using hot air at 100–150° C.

1-Stearoyl-2-[3-(benzyloxycarbonylamino)propanoyl]-sn-glycero-3-phosphocholine

White wax. Yield 70%. TLC analysis: One spot. $R_f$ 0.55 $^1H$ NMR ($CDCl_3$), δ (ppm): 0.83–0.89 (t, 3H), 1.23–1.27 (broad s, 28H), 1.54 (m, 2H), 2.22–2.29 (t, 2H), 2.53–2.56 (m, 2H), 3.15 (s, 9H), 3.41–3.44 (m, 2H), 3.60–3.63 (m, 2H), 3.85–3.96 (m, 2H), 4.13–4.25 (m, 4H), 5.05 (s, 2H), 5.20 (m, 1H), 7.27–7.33 (m, 5H).

1-Stearoyl-2-[4-(benzyloxycarbonylamino)butanoyl]-sn-glycero-3-phosphocholine

White wax. Yield 70%. TLC analysis: One spot. $R_f$ 0.55. $^1H$ NMR ($CDCl_3$), δ (ppm): 0.84–0.88 (t, 3H), 1.25 (broad s, 28H), 1.52–1.55 (m, 2H), 1.72–1.80 (m, 2H), 2.23–2.32 (m, 4H), 3.07–3.14 (m, 2H), 3.18 (s, 9H), 3.61–3.65 (m, 2H), 3.86–3.94 (m, 2H), 4.10–4.25 (m, 4H), 5.06 (s, 2H), 5.22 (m, 1H), 7.26–7.33 (m, 5H).

1-Stearoyl-2-[5-(benzyloxycarbonylamino)valeroyl]-sn-glycero-3-phosphocholine

White wax. Yield 70%. TLC analysis: One spot. $R_f$ 0.55. $^1H$ NMR ($CDCl_3$), δ (ppm): 0.84–0.89 (t, 3H), 1.26 (broad s, 28H), 1.54–1.65 (m, 4H), 1.72–1.77 (m, 2H), 2.23–2.30 (m, 4H), 3.07–3.12 (m, 2H), 3.16 (s, 9H), 3.61–3.65 (m, 2H), 3.86–3.94 (m, 2H), 4.10–4.25 (m, 4H), 5.06 (s, 2H), 5.20 (m, 1H), 7.26–7.33 (m, 5H).

1-Stearoyl-2-[6-(benzyloxycarbonylamino)hexanoyl]-sn-glycero-3-phosphocholine

White wax. Yield 65%. TLC analysis: One spot. $R_f$ 0.55. $^1H$ NMR ($CDCl_3$), δ (ppm): 0.84–0.89 (t, 3H), 1.24 (broad s, 28H), 1.30–1.62 (several m, 8H), 2.22–2.30 (m, 4H), 3.06–3.12 (m, 2H), 3.15 (s, 9H), 3.61–3.65 (m, 2H), 3.88–3.97 (m, 2H), 4.10–4.25 (m, 4H), 5.05 (s, 2H), 5.20 (m, 1H), 7.25–7.32 (m, 5H).

1-Stearoyl-2-[8-(benzyloxycarbonylamino)octanoyl]-sn-glycero-3-phosphocholine

White wax. Yield 65%. TLC analysis: One spot. $R_f$ 0.55. $^1H$ NMR ($CDCl_3$), δ (ppm): 0.84–0.89 (t, 3H), 1.25 (broad s, 28H), 1.30–1.33 (m, 6H), 1.46–1.49 (m, 2H), 1.52–1.58 (m, 4H), 2.22–2.29 (m, 4H), 3.05–3.10 (m, 2H), 3.17 (s, 9H), 3.61–3.65 (m, 2H), 3.85–3.96 (m, 2H), 4.10–4.23 (m, 4H), 5.06 (s, 2H), 5.20 (m, 1H), 7.22–7.29 (m, 5H).

1-Stearoyl-2-[12-(benzyloxycarbonylamino)dodecanoyl]-sn-glycero-3-phosphocholine White solid. Yield 60%. TLC analysis: One spot. $R_f$ 0.53. $^1H$ NMR ($CDCl_3$), δ (ppm): 0.84–0.88 (t, 3H), 1.23 (broad s, 28H), 1.30 (broad s, 14H), 1.45–1.50 (m, 4H), 1.53–1.59 (m, 2H), 2.23–2.50 (m, 4H), 3.06–3.12 (m, 2H), 3.17 (s, 9H), 3.62–3.67 (m, 2H), 3.84–3.94 (m, 2H), 4.10–4.25 (m, 4H), 5.05 (s, 2H), 5.20 (m, 1H), 7.23–7.30 (m, 5H).

Stage 4. Removal of the Protecting Benzyloxycarbonyl Group.

The obtained 1-stearoyl-2-[(benzyloxycarbonylamino) acyl]-3-phosphocholine (0.0025 mol) is dissolved in a mixture of 100 ml methanol and 5 ml acetic acid. The solution is introduced into round bottom double neck flask (200 ml) equipped with a magnetic stirrer, under an atmosphere of argon. Pd/C (0.5 g) is added to the solution and hydrogen is blown through the reaction mixture for 4 hours. The reaction proceeding is monitored by TLC analysis under the following conditions: silica gel 60 on aluminum sheet, eluent is the mixture of chloroform/methanol/water (65:35:5, v/v), indicator is a spray of the composition: p-methoxybenzaldehyde (10 ml), absolute ethanol (200 ml), 98% sulfuric acid (10 ml) and glacial acetic acid (2 ml). The chromatogram is sprayed with the indicator and then charred using hot air at 100–150° C.

The reaction assumed to be complete and hydrogenation is stopped after all corresponding 1-stearoyl-2-[(benzyloxycarbonylamino)acyl]-sn-glycero-phosphocholine has disappeared. The reaction mixture is then filtered through celete to remove the Pd/C, evaporated at 30° C., under vacuum. The crude residue is washed with ether (3×30 ml) and dried in a vacuum overnight. Conditions of the TLC analysis are the same as indicated above.

1-Stearoyl-2-(3-aminopropanoyl)-sn-glycero-3-phosphocholine, acetic

White wax. Yield 70%. TLC analysis: One spot. $R_f$ 0.2. $^1H$ NMR ($CD_3OD$), δ (ppm): 0.87–0.92 (t, 3H), 1.28 (broad s, 28H), 1.58–1.61 (m, 2H), 1.92 (s, 3H), 2.30–2.38 (t, 2H), 2.71–2.77 (t, 2H), 3.17–3.19 (m, 2H), 3.22 (s, 9H), 3.62–3.65 (m, 2H), 3.87–4.48 (several m, 6H), 5.24 (m, 1H). $^{31}P$ NMR ($CD_3OD$), δ (ppm): 0.01 (s). Chemical analysis: $C_{29}H_{59}N_2O_8P.CH_3COOH$. Calculated: C, 56.88%; H, 9.63%; N, 4.28%; P, 4.74%. Found: C, 57.01%; H, 10.11%; N, 4.18%; P, 4.52%.

1-Stearoyl-2-(4-aminobutanoyl)-sn-glycero-3-phosphocholine, acetate

White wax. Yield 70%. TLC analysis: One spot. $R_f$ 0.2. $^1H$ NMR ($CD_3OD$), δ (ppm): 0.86–0.92 (t, 3H), 1.28 (broad s, 28H), 1.56–1.60 (m, 2H), 1.94 (s, 3H), 1.96–1.99 (m, 2H), 2.29–2.35 (t, 2H), 2.46–2.52 (m, 2H), 2.95–3.02 (t, 2H), 3.22 (s, 9H), 3.62–3.66 (m, 2H), 3.87–4.46 (several m, 6H), 5.21–5.22 (m, 1H). $^{31}P$ NMR ($CD_3OD$), δ (ppm): 0.01 (s). Chemical analysis: $C_{30}H_{61}N_2O_8P.CH_3COOH$. Calculated: C, 57.48%; H, 9.73%; N, 4.19%; P, 4.64%. Found: C, 57.12%; H, 9.55%; N, 4.22%; P, 4.38%.

1-Stearoyl-2-(5-aminovaleroyl)-sn-glycero-3-phosphocholine, acetate

White wax. Yield 70%. TLC analysis: One spot. $R_f$ 0.2. $^1H$ NMR ($CD_3OD$), δ (ppm): 0.87–0.92 (t, 3H), 1.27 (broad s, 28H), 1.55–1.61 (m, 2H), 1.92 (s, 3H), 1.96–2.10 (m, 2H), 2.29–2.35 (t, 2H), 2.46–2.52 (m, 2H), 2.95–3.02 (t, 2H), 3.22 (s, 9H), 3.62–3.66 (m, 2H), 3.85–4.46 (several m, 6H), 5.19–5.21 (m, 1H). $^{31}P$ NMR ($CD_3OD$), δ (ppm): 0.01 (s). Chemical analysis: $C_{31}H_{63}N_2O_8P.CH_3COOH$. Calculated: C, 58.06%; H, 9.82%; N, 4.05%; P, 4.54%. Found: C, 57.90%; H, 10.01%; N, 4.20%; P, 4.48%.

1-Stearoyl-2-(6-aminohexanoyl)-sn-glycero-3-phosphocholine, acetate

White wax. Yield 65%. TLC analysis: One spot. $R_f$ 0.2. $^1H$ NMR ($CD_3OD$), δ (ppm): 0.86–0.92 (t, 3H), 1.28 (broad s, 28H), 1.32–1.50 (m, 2H), 1.56–1.72 (broad m, 6H), 1.91 (s, 3H), 2.28–2.40 (broad m, 4H), 2.88–2.94 (t, 2H), 3.22 (s, 9H), 3.61–3.66 (m, 2H), 3.95–4.08 (m, 2H), 4.10–4.38 (several m, 4H), 5.24 (m, 1H). $^{31}P$ NMR ($CD_3OD$), δ (ppm): 0.01 (s). Chemical analysis: $C_{32}H_{65}N_2O_8P.CH_3COOH$. Calculated: C, 58.62%; H, 9.91%; N, 4.02%; P, 4.45%. Found: C, 58.19%; H, 10.11%; N, 4.12%; P, 4.58%.

1-Stearoyl-2-(8-aminooctanoyl)-sn-glycero-3-phosphocholine, acetate

White wax. Yield 65%. TLC analysis: One spot. $R_f$ 0.2. $^1H$ NMR ($CD_3OD$), δ (ppm): 0.86–0.92 (t, 3H), 1.28 (broad s, 28H), 1.37 (s, 6H), 1.59–1.67 (broad m, 6H), 1.93 (s, 3H), 2.28–2.39 (broad m, 4H), 2.86–2.92 (t, 2H), 3.22 (s, 9H), 3.62–3.66 (m, 2H), 3.97–4.03 (m, 2H), 4.13–4.39 (several m, 4H), 5.22–5.23 (m, 1H). $^{31}P$ NMR ($CD_3OD$), δ (ppm): 0.01 (s). Chemical analysis: $C_{34}H_{69}N_2O_8P.CH_3COOH$. Calculated: C, 59.67%; H, 10.08%; N, 3.87%; P, 4.28%. Found: C, 59.22%; H, 10.21%; N, 3.99%; P, 4.08%.

1-Stearoyl-2-(12-aminododecanoyl)-sn-glycero-3-phosphocholine, acetate

White solid. Yield 60%. TLC analysis: One spot. $R_f$ 0.2. $^1H$ NMR ($CD_3OD$), δ (ppm): 0.85–0.90 (t, 3H), 1.28 (s, 28H), 1.36 (broad s, 14H), 1.56–1.68 (m, 6H), 1.94 (s, 3H), 2.29–2.39 (m, 4H), 2.85–2.90 (m, 2H), 3.20 (s, 9H), 3.60–3.66 (m, 2H), 3.95–4.03 (m, 2H), 4.12–4.37 (several m, 4H), 5.21–5.23 (m, 1H). $^{31}P$ NMR ($CD_3OD$), δ (ppm): 0.01 (s). Chemical analysis: $C_{40}H_{81}N_2O_{10}P.CH_3COOH$. Calculated: C, 61.54%; H, 10.38%; N, 3.59%; P, 3.97%. Found: C, 61.36%; H, 10.69%; N, 3.41%; P, 3.85%.

Stage 5. Preparation of free 1-acyl-2-[n-(aminoacyl)-sn-glycero-3-phosphocholine The solution of acetic acid and the corresponding 1-acyl-2-[n-(aminoacyl)-sn-glycero-3-phosphocholine complex (1.36 mmol) in methylene chloride (30 ml) is introduced into a single neck round bottom flask (150 ml) equipped with a magnetic stirrer. Triethylamine (0.3 ml, 3 mmol) is added to this solution. The resulting reaction mixture is stirred at room temperature for 30 min. During this procedure the free 2-amino-acyl lipid is formed. The reaction solution with the obtained free 2-amino-acyl lipid is used for the following synthesis without any additional processing.

Stage 6. Preparation of 1-acyl-(2-n-arylacetamidoacyl)-sn-glycero-3-phosphocholine A mixture of the corresponding drug, in this case diclofenac [o-[(2,6-dichlorophenyl)amino]phenyl]acetic acid] (1.36 mmol), triphenylphosphine (0.72 g., 2.75 mmol) and aldritiol-2 (0.6 g., 2.75 mmol) is introduced, under an inert atmosphere of argon, into a reaction flask containing the solution of free 2-amino-acyl lipid in methylene chloride (see stage 5). The reaction solution immediately becomes yellow and is left stirring for one hour at room temperature in an atmosphere of argon. The solvent is then removed by evaporation and the product is extracted and purified by a flash column chromatography by varying the composition of the mobile phase. For extracting and purifying 1 g. of solid reaction mixture, 35 g. of silica gel 60 (230–400 mesh ASTM) in a glass column (40×2 cm) with a pressure of about 1.5 atm., was used. The first fraction of eluent is 150 ml of a mixture of chloroform with methanol (65:35, v/v). The second fraction of eluent is 250 ml of a mixture of chloroform, methanol and water (65:35:5, v/v). In the first fraction the main impurities are removed, and in the second fraction the fine purification of the final product, i.e. the phospholipid-drug conjugate, is realized.

Lipid Derivatives of Diclofenac (DP-DFC)

All the synthesized products mentioned below are pale yellow solids that when analyzed by TLC are displayed in one bright red spot, $R_f$ is 0.3. The TLC analysis conditions are as follows: Silica gel 60 on aluminum sheet. Eluent is chloroform:methanol:water (65:35:5, v/v). Indicator is a spray of the composition: 4-methoxybenzaldehyde (10 ml), absolute ethanol (200 ml), 98% sulfuric acid (10 ml) and glacial acetic acid (2 ml). The chromatogram is sprayed with the indicator and then charred at 100° C.

1-Stearoyl-2-{3-[2-(2,6-dichloroanilino)phenylacetamido]propanoyl}-sn-glycero-3-phosphocholine

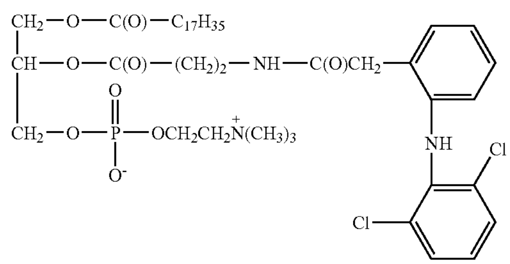

Yield 75%. $^1$H NMR ($CD_3OD$), δ (ppm): 0.84–0.89 (t, 3H), 1.26 (broad s, 28H), 1.54–1.59 (m, 2H), 2.27–2.33 (t, 2H), 2.56–2.61 (t, 2H), 3.18 (s, 9H), 3.44–3.49 (t, 2H), 3.58–3.61 (m, 2H), 3.68 (s, 2H), 4.02–4.05 (m, 2H), 4.19–4.26 (m,3H), 4.36–4.38 (m, 1H), 5.21–5.25 (m. 1H), 6.36–6.40 (d, 1H), 6.84–6.90 (t, 1H), 7.02–7.09 (m,2H), 7.20–7.24 (d, 1H), 7.37–7.41 (d, 2H). $^{31}$P NMR ($CD_3OD$), δ (ppm): −0.84 (s). Chemical analysis: $C_{43}H_{68}N_3O_9PCl_2.2H_2O$. Calculated: C, 56.83%; H, 7.93%; N, 4.62%; P, 3.41%. Found: C, 57.01%; H, 7.59%; N, 4.27%; P, 3.39%.

1-Stearoyl-2-{4-[2-(2,6-dichloroanilino)phenylacetamido]butanoyl}-sn-glycero-3-phosphocholine

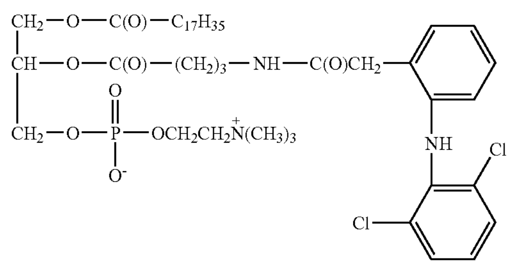

Yield 75%. $^1$H NMR ($CD_3OD$), δ (ppm): 0.86–0.90 (t, 3H), 1.25 (broad s, 28H), 1.53–1.57 (m, 2H), 1.80–1.84 (m, 2H), 2.27–2.31 (t, 2H), 2.36–2.41 (t, 2H), 3.17 (s, 9H), 3.19–3.25 (m, 2H), 3.57–3.60 (m, 2H), 3.66 (s, 2H), 4.00–4.03 (m, 2H), 4.17–4.25 (m, 3H), 4.37–4.41 (m, 1H), 5.21–5.25 (m, 1H), 6.37–6.40 (d, 1H), 6.85–6.89 (t, 1H), 7.01–7.07 (m, 2H), 7.19–7.22 (d, 1H), 7.37–7.40 (d, 2H). $^{31}$P NMR ($CD_3OD$), δ (ppm): −0.88 (s). MS: $C_{44}H_{70}N_3O_9PCl_2$, Found m/e: 886.9 (FAB) (main pick). Chemical analysis: $C_{44}H_{70}N_3O_9PCl_2.2H_2O$. Calculated: C, 57.27%; H, 8.03%; N, 4.56%; P, 3.36%. Found: C, 57.21%; H, 8.11%; N, 4.61%; P, 3.32%.

1-Stearoyl-2-{5-[2-(2,6-dichloroanilino)phenylacetamido]valeroyl}-sn-glycero-3-phosphocholine

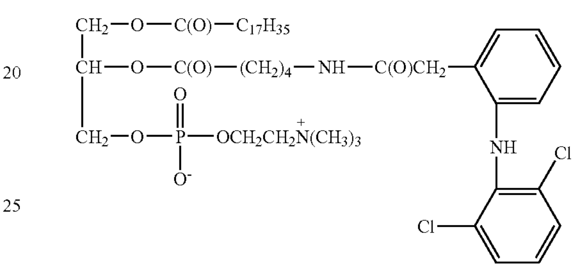

Yield 75%. $^1$H NMR ($CD_3OD$), δ (ppm): 0.83–0.89 (t, 3H), 1.24 (broad s, 28H), 1.54–1.64 (broad m, 6H), 2.26–2.34 (m, 4H), 3.18–3.23 (m, 11H), 3.58–3.62 (m, 2H), 3.66 (s, 2H), 4.00–4.03 (m, 2H), 4.16–4.25 (m, 3H), 4.36–4.38 (m, 1H), 5.21–5.25 (m, 1H), 6.36–6.40 (d, 1H), 6.87–6.89 (t, 1H), 7.02–7.08 (m, 2H), 7.19–7.22 (d, 1H), 7.37–7.40 (d, 2H). $^{31}$P NMR ($CD_3OD$), δ (ppm): −0.92 (s). Chemical analysis: $C_{45}H_{72}N_3O_9PCl_2$. Calculated: C, 60.00%; H, 8.00%; N, 4.66%; P, 3.44%; Cl, 7.88%. Found: C, 59.64%; H, 8.28%; N, 4.69%; P, 3.54%; Cl, 7.66%.

1-Stearoyl-2-{6-[2-(2,6-dichloroanilino)phenylacetamido]hexanoy}-sn-glycero-3-phosphocholine

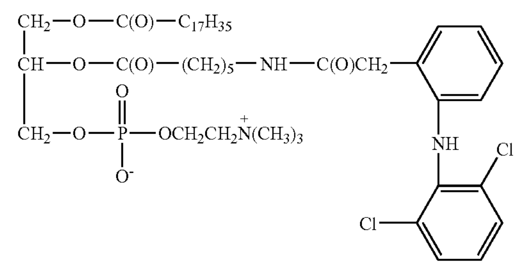

Yield 80%. $^1$H NMR ($CD_3OD$), δ (ppm): 0.85–0.90 (t, 3H), 1.26–1.35 (broad s, 30H), 1.50–1.61 (m, 6H), 2.26–2.34 (m, 4H), 3.16–3.22 (m, 11H), 3.59–3.66 (m, 4H), 4.00–4.02 (m, 2H), 4.19–4.26 (several m, 3H), 4.38–4.40 (m, 1H), 5.21–5.25 (m, 1H), 6.37–6.40 (d, 1H), 6.83–6.90 (t 1H), 6.99–7.07 (several m, 2H), 7.18–7.22 (d, 1H), 7.37–7.41 (d, 2H). $^{31}$P NMR ($CD_3OD$), δ (ppm): −0.92 (s). Chemical analysis: $C_{46}H_{74}N_3O_9PCl_2.2H_2O$. Calculated: C, 58.10%; H, 8.21%; N, 4.42%; P, 3.26%. Found: C, 58.31%; H, 8.36%; N, 4.11%; P, 3.30%.

1-Stearoyl-2-{8-[2-(2,6-dichloroanilino)phenylacetamido]octanoyl}-sn-glycero-3-phosphocholine

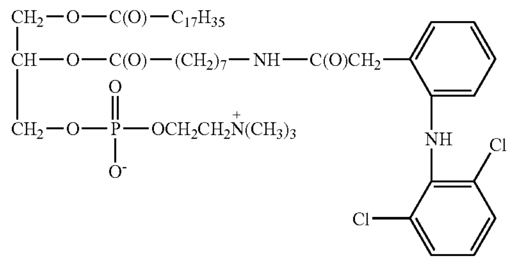

Yield 80%. $^1$H NMR ($CD_3OD$), δ (ppm): 0.85–0.91 (t, 3H), 1.26–1.30 (broad s, 34H), 1.51–1.60 (m, 6H), 2.26–2.34 (m, 4H), 3.16–3.22 (m, 11H), 3.60–3.65 (m, 4H), 3.96–4.02 (m, 2H), 4.16–4.27 (several m, 3H), 4.38–4.40 (m, 1H), 5.19–5.24 (m, 1H), 6.36–6.40 (d, 1H), 6.83–6.90 (t, 1H), 6.99–7.09 (several m, 2H), 7.18–7.22 (d, 1H), 7.37–7.41 (d, 2H). $^{31}$P NMR ($CD_3OD$), δ (ppm): −0.91 (s). Chemical analysis: $C_{48}H_{78}N_3O_9PCl_2.2H_2O$. Calculated: C, 58.90%; H, 8.380%; N, 4.29%; P, 3.16%. Found: C, 59.19%; H, 8.39%; N, 4.19%; P, 3.20%.

1-Stearoyl-2-{12-[2-(2,6-dichloroanilino)phenylacetamido]dodecanoyl}-sn-glycero-3-phosphocholine

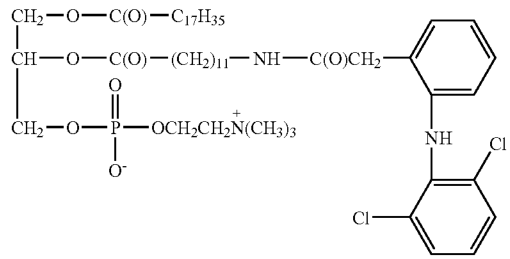

Yield 70%. $^1$H NMR ($CD_3OD$), δ (ppm): 0.87–0.92 (t, 3H), 1.28 (broad s, 42H), 1.49–1.62 (broad m, 6H), 2.28–2.36 (m, 4H), 3.16–3.22 (m+s, 11H), 3.62–3.66 (m+s, 4H), 3.98–4.03 (t, 2H), 4.18–4.29 (m, 3H), 4.41–4.42 (d, 1H), 5.20 (broad m, 1H), 6.37–6.41 (d, 1H), 6.87–6.90 (t, 1H), 7.02–7.10 (m, 2H), 7.19–7.22 (d, 1H), 7.39–7.42 (d, 2H). $^{31}$P NMR ($CD_3OD$), δ (ppm): −1.71 (s). Chemical analysis: $C_{52}H_{86}N_3O_9PCl_2.H_2O$. Calculated: C, 61.42%; H, 8.66%; N, 4.13%; P, 3.05%. Found: C, 61.33%; H, 9.07%; N, 4.18%; P, 2.85%.

Example 2

Preparation of Lipid Derivatives of Indomethacin (DP-Indo)

The procedure for the preparation of lipid derivatives of indomethacin (1-(p-chlorobenzoyl)-5-methoxy-2-methyl-3-indolylacetic acid) is the same as the process outlined in Example 1, steps 1 to 6, except that in step 6 instead of diclofenac the drug included in the reaction mixture is indomethacin.

Lipid Derivatives of Indomethacin (DP-Indo)

The synthesized compounds were subjected to TLC analysis under the following conditions: Silica gel 60 on aluminum sheet. Eluent is chloroform:methanol:water (65:35:5, v/v). Indicator is a spray of the composition: 4-methoxybenzaldehyde (10 ml), absolute ethanol (200 ml), 98% sulfuric acid (10 ml) and glacial acetic acid (2 ml). The chromatogram is sprayed with the indicator and then charred at 100° C.

1-Stearoyl-2-{3-[1-(p-chlorobenzoyl)-5-methoxy-2-methyl-3-indolylacetamido]propanoyl}-sn-glycero-3-phosphocholine

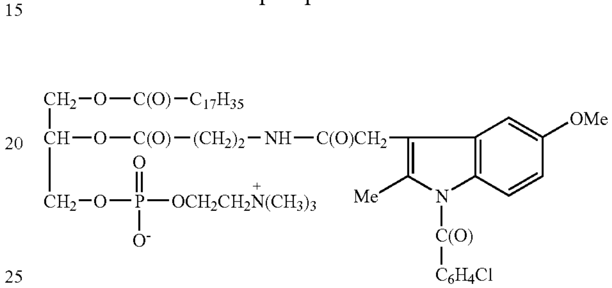

Pale yellow wax. Yield 80%. TLC analysis: One spot. $R_f$ is 0.35. $^1$H NMR ($CD_3OD$), δ (ppm): 0.85–0.91 (t, 3H), 1.26–1.30 (broad s, 28H), 1.52–1.55 (m, 2H), 2.25–2.31 (m, 5H), 2.54–2.60 (t, 2H), 3.18 (m, 9H), 3.43–3.46 (t, 2H), 3.57–3.62 (m, 4H), 3.81 (s, 3H), 3.98–4.02 (m, 2H), 4.13–4.25 (several m, 4H), 5.16 (m, 1H), 6.64–6.69 (d, 1H), 6.92–6.95 (d, 1H), 7.00 (s, 1H), 7.54–7.58 (d, 2H), 7.67–7.72 (d, 2H). $^{31}$P NMR ($CD_3OD$), δ (ppm): −0.13 (s). Chemical analysis: $C_{48}H_{73}N_3O_{11}PCl.2H_2O$. Calculated: C, 59.41%; H, 7.94%, N, 4.33%; P, 3.20%; Cl, 3.66%. Found: C, 59.79%; H, 7.96%; N, 3.91%; P, 3.28%, Cl, 3.60%.

1-Stearoyl-2-{4-[1-(p-chlorobenzoyl)-5-methoxy-2-methyl-3-indolylacetamido]butanoyl}-sn-glycero-3-phosphocholine

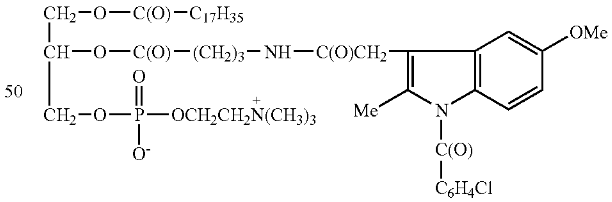

Pale yellow wax. Yield 80%. TLC analysis: One spot. $R_f$ is 0.35. $^1$H NMR ($CD_3OD$), δ (ppm): 0.85–0.91 (t, 3H), 1.26 (broad s, 28H), 1.52–1.55 (m, 2H), 1.77–1.83 (m, 2H), 2.24–2.39 (m, 7H), 3.18 (s, 9H), 3.21–3.29 (m, 2H), 3.57–3.60 (m, 4H), 3.80–3.81 (s, 3H), 3.98–4.01 (m, 2H), 4.15–4.36 (several m, 4H), 5.19–5.20 (m, 1H), 6.64–6.69 (d, 1H), 6.92–6.96 (d, 1H), 7.00 (s, 1H), 7.54–7.57 (d, 2H), 7.67–7.72 (d, 2H). $^{31}$P NMR ($CD_3OD$) δ (ppm): −0.08 (s). Chemical analysis: $C_{49}H_{75}N_3O_{11}PCl.H_2O$. Calculated: C, 60.90%; H, 7.98%; N, 4.27%; P, 3.15%; Cl, 3.67%. Found: C, 60.82%; H, 8.35%; N, 4.27%; P, 3.10%; Cl, 3.60%.

1-Stearoyl-2-{5-[1-(p-chlorobenzoyl)-5-methoxy-2-methyl-3-indolylacetamido]valeroyl}-sn-glycero-3-phosphocholine

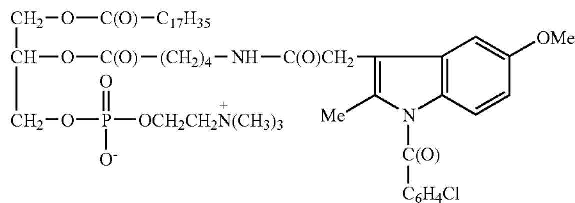

Pale yellow wax. Yield 80%. TLC analysis: One spot. $R_f$ is 0.35. $^1$H NMR ($CD_3OD$), δ (ppm): 0.85–0.91 (t, 3H), 1.26 (s, 28H), 1.53–1.60 (m, 6H), 2.25–2.36 (m, 7H), 3.21 (s, 9H), 3.58–3.62 (m, 4H), 3.87–3.80 (s, 3H), 3.98–4.01 (m, 2H), 4.15–4.24 (several m, 3H), 4.35–4.37 (two d, 1H), 5.20–5.21 (m, 1H), 6.64–6.68 (d, 1H), 6.92–6.96 (d, 1H), 7.00 (s, 1H), 7.54–7.57 (d, 2H), 7.67–7.72 (d, 2H) $^{31}$P NMR ($CD_3OD$), δ (ppm): −0.07(s). Chemical analysis: $C_{50}H_{77}N_3O_{11}PCl.2H_2O$. Calculated: C, 60.15%; H, 8.12%; N, 4.21%; P, 3.11%; Cl, 3.56%. Found: C, 60.39%; H, 8.33%; N, 4.08%; P, 3.05%; Cl, 3.50%.

1-Stearoyl-2-{6-[1-(p-chlorobenzoyl)-5-methoxy-2-methyl-3-indolylacetamido]hexanoyl}-sn-glycero-3-phosphocholine

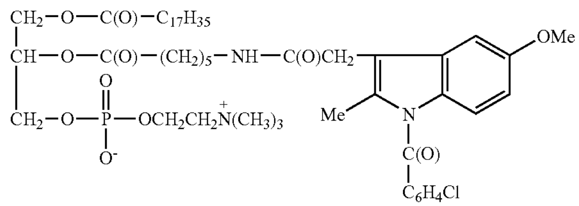

Pale yellow wax. Yield 80%. TLC analysis: One spot. $R_f$ is 0.38. $^1$H NMR ($CD_3OD$), δ (ppm): 0.85–0.91 (t, 3H), 1.26 (broad s, 30H), 1.48–1.62 (m, 6H), 2.26–2.32 (m, 7H), 3.15–3.19 (m, 11H), 3.59–3.62 (m, 4H), 3.80 (s, 3H), 3.96–4.01 (t, 2H), 4.16–4.25 (m, 3H), 4.36–4.38 (two d, 1H), 5.20–5.21 (m, 1H), 6.64–6.69 (d, 1H), 6.91–6.95 (d, 1H), 7.01 (s, 1H), 7.53–7.58 (d, 2H), 7.68–7.71 (d, 2H) $^{31}$P NMR ($CD_3OD$), δ (ppm): −0.07(s). Chemical analysis: $C_{51}H_{79}N_3O_{11}PCl.H_2O$. Calculated: C, 61.60%; H, 8.20%; N, 4.22%; P, 3.12%; Cl, 3.57%. Found: C, 60.08%; H, 8.35%; N, 4.27%; P, 3.22%; Cl, 3.60%.

1-Stearoyl-2-{8-[1-(p-chlorobenzoyl)-5-methoxy-2-methyl-3-indolylacetamido]octanoyl}-sn-glycero-3-phosphocholine

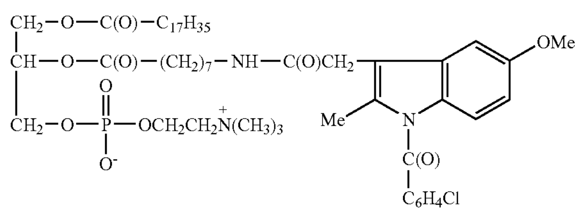

Pale yellow wax. Yield 80%. TLC analysis: One spot. $R_f$ is 0.38. $^1$H NMR ($CD_3OD$), δ (ppm): 0.85–0.91 (t, 3H), 1.26 (broad s, 34H), 1.51–1.57 (m, 6H), 2.26–2.33 (m, 7H) 3.16–3.20 (m, 11H), 3.58–3.63 (m, 4H), 3.80 (s, 3H), 3.96–4.02 (t, 2H), 4.16–4.26 (m, 3H), 4.39–4.41 (two d, 1H), 5.21 (m, 1H), 6.64–6.69 (d, 1H), 6.91–6.95 (d, 1H), 7.01 (s, 1H), 7.53–7.58 (d, 2H), 7.68–7.71 (d, 2H) $^{31}$P NMR ($CD_3OD$), δ (ppm): −0.08(s). Chemical analysis: $C_{53}H_{83}N_3O_{11}PCl.2H_2O$. Calculated: C, 61.16%; H, 8.46%; N, 4.09%; P, 3.03%; Cl, 3.41%. Found: C, 61.21%; H, 8.37%; N, 4.04%; P, 2.98%; Cl, 3.47%.

Example 3

Preparation of Lipid Derivatives of Ibuprofen (DP-Ibu)

The procedure for the preparation of lipid derivatives of ibuprofen (2-(4-isobutylphenyl)propionic acid) is the same as the process outlined in Example 1, steps 1 to 6, except that in step 6 instead of diclofenac the drug included in the reaction mixture is ibuprofen.

Lipid Derivatives of Ibuprofen (DP-Ibu)

The synthesized compounds were subjected to TLC analysis under the following conditions: Silica gel 60 on aluminum sheet. Eluent is chloroform:methanol:water (65:35:5, v/v). Indicator is a spray of the composition: 4-methoxybenzaldehyde (10 ml), absolute ethanol (200 ml), 98% sulfuric acid (10 ml) and glacial acetic acid (2 ml). The chromatogram is sprayed with the indicator and then charred at 100° C.

1-Stearoyl-2-{3-[α-methyl-4-(2-methylpropyl)benzeneacetamido]propanoyl}-sn-glycero-3-phosphocholine

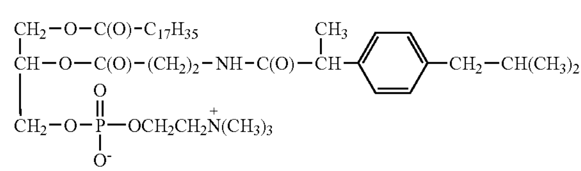

White wax. Hygroscopic. Yield 60%. TLC analysis: One spot. $R_f$ is 0.38. $^1$H NMR ($CD_3OD$), δ (ppm): 0.88–0.93 (m, 9H), 1.29 (s, 28H), 1.41–1.44 (d, 3H), 1.58–1.63 (m, 2H), 1.80–1.90 (m, 1H), 2.28–2.35 (t, 2H), 2.43–2.46 (d, 2H), 2.51–2.57 (t, 2H), 3.22 (s, 9H), 3.40–3.45 (m, 2H), 3.61–3.66 (m, 3H), 3.98–4.41 (several m, 6H), 5.18 (m, 1H), 7.01–7.07 (d, 2H), 7.22–7.26 (d, 2H). $^{31}$P NMR ($CD_3OD$), δ (ppm): −0.20(s). Chemical analysis: $C_{42}H_{75}N_2O_9P.4H_2O$. Calculated: C, 59.02%; H, 9.93%; N, 3.28%; P, 3.63%. Found: C, 59.26%; H, 9.64%; N, 3.43%; P, 3.65%.

1-Stearoyl-2-{6-[α-methyl-4-(2-methylpropyl)benzeneacetamido]hexanoyl}-sn-glycero-3-phosphocholine

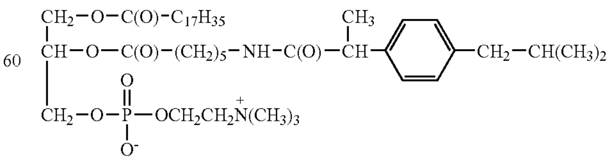

White wax. Hygroscopic. Yield 50%. TLC analysis: One spot. $R_f$ is 0.38. $^1$H NMR ($CD_3OD$), δ (ppm): 0.88–0.93 (m, 9H), 1.29 (broad s, 31H), 1.40–1.48 (m+d, 6H), 1.55–1.62

(m, 4H), 1.78–1.90 (m, 1H), 2.27–2.35 (m, 4H), 2.43–2.46 (d, 2H), 3.11–3.16 (m, 2H), 3.22 (s, 9H), 3.56–3.66 (m, 3H), 4.00–4.03 (t, 2H), 4.18–4.28 (several m, 4H), 5.18 (m, 1H), 7.07–7.11 (d, 2H), 7.22–7.25 (d, 2H). $^{31}$P NMR ($CD_3OD$), δ (ppm): −0.20(s). Chemical analysis: $C_{45}H_{81}N_2O_9P.2.5H_2O$. Calculated: C, 62.07%; H, 9.89%; N, 3.22%; P, 3.56%. Found: C, 62.00%; H, 10.01%; N, 3.32%; P, 3.19%.

Example 4

Preparation of Lipid Derivatives of Naproxen (DP-Nap)

The procedure for the preparation of lipid derivatives of naproxen (d-2-(6-methoxy-2-naphthyl)propionic acid) is the same as the process outlined in Example 1, steps 1 to 6, except that in step 6 instead of diclofenac the drug included in the reaction mixture is naproxen.

Lipid Derivatives of Naproxen (DP-Nap)

The synthesized compounds were subjected to TLC analysis under the following conditions: Silica gel 60 on aluminum sheet. Eluent is chloroform:methanol:water (65:35:5 v/v). Indicator is a spray of the composition: 4-methoxybenzaldehyde (10 ml), absolute ethanol (200 ml), 98% sulfuric acid (10 ml) and glacial acetic acid (2 ml). The chromatogram is sprayed with the indicator and then charred at 100° C.

1-Stearoyl-2-{3-[(S)-6-methoxy-α-methyl-2-naphtaleneacetamido]propanoyl}-sn-glycero-3-phosphocholine

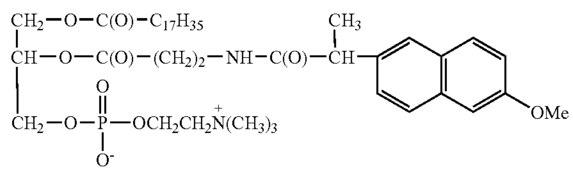

White wax. Hygroscopic. Yield 65%. TLC analysis: One spot. $R_f$ is 0.38. $^1$H NMR ($CD_3OD$), δ (ppm): 0.86–0.91 (t, 3H), 1.26 (s, 28H), 1.50–1.53 (m, 5H), 2.23–2.29 (t, 2H), 2.51–2.57 (t, 2H), 3.16 (s, 9H), 3.41–3.46 (t, 2H), 3.56–3.60 (m, 2H), 3.78–3.80 (m, 1H), 3.88 (s, 3H), 3.97–4.02 (m, 2H), 4.12–4.31 (several m, 4H), 5.17–5.20 (m, 1H), 7.08–7.13 (d, 1H), 7.19 (s, 1H), 7.41–7.45 (d, 1H), 7.70–7.73 (m, 3H). $^{31}$P NMR ($CD_3OD$), δ (ppm): −0.17(s). Chemical analysis: $C_{43}H_{71}N_2O_{10}P.4H_2O$. Calculated: C, 58.37%; H, 8.93%; N, 3.17%; P, 3.50%, Found: C, 58.34%; H, 8.98%; N, 3.25%; P, 3.58%.

1-Stearoyl-2-{4-[(S)-6-methoxy-α-methyl-2-naphtaleneacetamido]butanoyl}-sn-glycero-3-phosphocholine

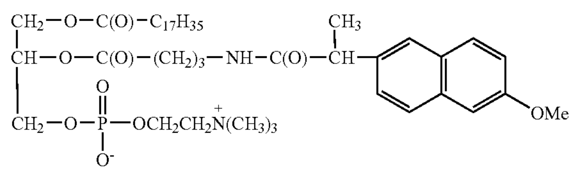

White wax. Hygroscopic. Yield 65%. TLC analysis: One spot. $R_f$ is 0.38. $^1$H NMR ($CD_3OD$), δ (ppm): 0.86–0.91 (t, 3H), 1.26 (s, 30H), 1.50–1.53 (m, 5H), 1.73–1.82 (m, 2H), 2.26–2.33 (m, 4H), 3.17 (s, 11H), 3.56–3.60 (m, 2H), 3.75–3.78 (m, 1H), 3.88 (s, 3H), 3.97–4.02 (m, 2H), 4.12–4.31 (several m, 4H 5.17–5.20 (m, 1H), 7.08–7.13 (d, 1H), 7.19 (s, 1H), 7.41–7.45 (d, 1H), 7.70–7.73 (m, 3H). $^{31}$P NMR ($CD_3OD$), δ (ppm): −0.22(s). Chemical analysis: $C_{44}H_{73}N_2O_{10}P.5H_2O$. Calculated: C, 58.10%; H, 9.12%; N, 3.08%; P, 3.40%. Found: C, 58.69%; H, 9.24%; N, 3.18%; P, 3.40%.

1-Stearoyl-2-{6-[(S)-6-methoxy-α-methyl-2-naphtaleneacetamido]hexanoyl}-sn-glycero-3-phosphocholine

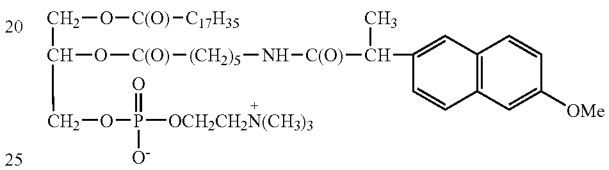

White wax. Hygroscopic. Yield 65%. TLC analysis: One spot. $R_f$ is 0.38. $^1$H NMR ($CD_3OD$), δ (ppm): 0.87–0.91 (t, 3H), 1.26 (broad s, 32H), 1.44–1.57 (several m, 10H), 2.23–2.31(m, 4H), 3.14–3.20 (s, 9H), 3.60–3.62 (m, 2H), 3.75–3.78 (m, 1H), 3.88 (s, 3H), 4.00–4.02 (m, 2H), 4.17–4.38 (several m, 4H), 5.22 (m, 1H), 7.09–7.12 (d, 1H), 7.19 (s, 1H), 7.43–7.46 (d, 1H), 7.70–7.73 (m, 3H). $^{31}$P NMR ($CD_3OD$), δ (ppm): −0.80(s). Chemical analysis: $C_{46}H_{77}N_2O_{10}P.2H_2O$. Calculated: C, 62.44%; H, 9.16%; N, 3.17%; P, 3.50%. Found: C, 62.73%; H, 9.41%; N, 3.29%; P, 3.49%.

Example 5

Preparation of Lipid Derivatives of 6-methoxy-2-naphthylacetic acid (DP-MNap)

The procedure for the preparation of lipid derivatives of 6-methoxy-2-naphthylacetic acid is the same as the process outlined in Example 1, steps 1 to 6, except that in step 6 instead of diclofenac the drug included in the reaction mixture is 6-methoxy-2-naphthylacetic acid.

6-methoxy-2-naphthylacetic acid was prepared according to the procedure described by Khorana and Pishawikar (Indian J. Pharm. (1961) 23: 297–301).

Yield was 60%.

The final products, i.e. the phospholipid-drug conjugates obtained at the end of step 6, were subjected to TLC analysis under the following conditions: Silica gel 60 on aluminum sheet. Eluent is chloroform:methanol:water (65:35:5 v/v). Indicator is a spray of the composition: 4-methoxybenzaldehyde (10 ml), absolute ethanol (200 ml), 98% sulfuric acid (10 ml) and glacial acetic acid (2 ml). The chromatogram is sprayed with the indicator and then charred at 100° C.

A lipid derivative of 6-methoxy-2-naphthylacetic acid (DP-MNap) is depicted bellow.

1-Stearoyl-2-{4-[2-(6-methoxynaphtyl)acetamido]butanoyl}-sn-glycero-3-phosphocholine

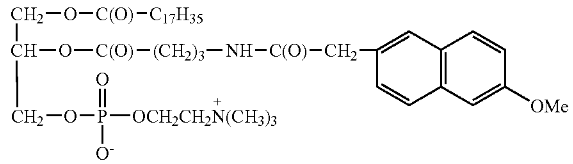

White solid. Yield 60%. TLC analysis: One spot. $R_f$ is 0.5. $^1H$ NMR ($CD_3OD$), δ (ppm): 0.87–0.92 (t, 3H), 1.27 (broad s, 28H), 1.53–1.56 (broad m, 2H), 1.78–1.84 (m, 2H), 2.25–2.40 (m, 4H), 3.15 (s, 9H), 3.21–3.27 (m, 2H), 3.54–3.58 (m, 2H), 3.62 (s, 2H), 3.90 (s, 3H), 4.00–4.04 (m, 2H), 4.18–4.23 (m, 3H), 4.36–4.41 (d, 1H), 5.20–5.24 (m, 1H), 7.09–7.14 (d, 1H), 7.21–7.22 (m, 1H), 7.36–7.40 (d, 1H), 7.67–7.75 (m, 3H). $^{31}P$ NMR ($CD_3OD$), δ (ppm): 0.83(s). Chemical analysis: $C_{43}H_{71}N_2O_{10}P.2H_2O$. Calculated: C, 61.28%; H, 8.90%; N, 3.32%; P, 3.68%. Found: C, 61.42%; H, 9.08%; N, 3.48%; P, 3.70%.

Example 6

Solubility Measurements of Lipid Derivatives of Diclofenac, Indomethacin, Ibuprofen, Naproxen and 6-methoxy-2-naphthylacetic acid The solubility of several lipid derivatives of diclofenac, indomethacin, ibuprofen, naproxen and 6-methoxy-2-naphthylacetic acid was determined at room temperature (22° C.) in aqueous solutions (water and saline) and in organic solutions (ethanol and octanol). In addition, the partition coefficient ($P_c$) values for these compounds, i.e their distribution ratios between the organic and the aqueous phases (octanol/saline), were calculated. The results, presented as the calculated Log $P_c$, are shown in Table 1.

The distribution of the compounds between the organic and the aqueous phases was measured by the shake-flask technique. Five milliliters of octanol containing about 3 mg of the studied compound were mixed with 5 ml saline. The mixture was shaken overnight at 22° C. before the octanol and saline phases were separated. One ml from each phase was dissolved into an appropriate volume of ethanol so that the optical absorption of the obtained solution is in range of 0.1 to 1.0.

The coefficient $P_c$ is calculated by the following ratio:

$$P_c = \frac{A_{oct} V_1 l_2}{A_{sal} V_2 l_1}$$

where $A_{oct}$ is the optical absorption, at $\lambda_{max}$, of the ethanol solution in which one ml of octanol phase is dissolved, $V_1$ is the volume of this ethanol solution and $l_1$ is the width (cm) of the cuvette used for measurement of the optical absorption.

$A_{sal}$ is the optical absorption, at $\lambda_{max}$, of the ethanol solution in which the one ml of saline phase is dissolved, $V_2$ is the volume of this ethanol solution and $l_2$ is the width (cm) of the cuvette used for measurement of the optical absorption.

Solubility values of the lipid derivatives of diclofenac, indomethacin, ibuprofen, naproxen and 6-methoxy-2-naphthylacetic acid in water and saline and their octanol/saline distributions are presented hereinbelow in table 1.

The tested lipid derivatives form suspensions or gel mixtures in water and saline. Solutions containing the lipid derivatives form suspensions or gel mixtures even after being filtrated through 0.45 μm filter.

Table 1. Water and Saline Solubility and Octanol/Saline Distribution Coefficient (log $P_c$) of Lipid Derivatives at 22° C.

Lipid derivatives have the structure: lyso-lecithin-linker-drug wherein the linker is —C(O)—$(CH_2)_n$—NH—, the drug is diclofenac (DCF), indomethacin (Indo), ibuprofen (Ibu), naproxen (Nap) or 6-methoxy-2-naphthylacetic acid (MNap).

| Lipid derivative | | Solubility (mg/ml) | | |
|---|---|---|---|---|
| Drug | n | Water | Saline | log $P_c$ |
| DCF | 2 | 0.003[a)] | 0.002[a)] | 2.8 ± 0.1 |
| DCF | 3 | 0.002[a)] | 0.002[a)] | ≧3 |
| DCF | 4 | 0.002[a)] | 0.002[a)] | ≧3 |
| DCF | 5 | 0.0015[b)] | 0.0015[b)] | ≧3 |
| DCF | 7 | 0.001[b)] | 0.001[b)] | ≧3 |
| DCF | 11 | <0.001[b)] | <0.001[b)] | ≧2.5 |
| Indo | 2 | less than 0.9[a)] | about 1.5[a)] | 2.5 |
| Indo | 3 | less than 0.6[a)] | about 1.5[a)] | 2.5 |
| Indo | 4 | less than 0.01[b)] | about 0.1[b)] | 2.9 |
| Indo | 5 | less than 0.01[b)] | about 0.01[b)] | 3.2 |
| Indo | 7 | about 0.005[b)] | — | 3.7 |
| Ibu | 2 | 0.2[a)] | 0.3[a)] | 1.8 |
| Ibu | 5 | 0.5[a)] | 0.5[a)] | ≧3 |
| Nap | 2 | 0.01[a)] | 0.06[a)] | ≧3 |
| Nap | 3 | 0.12[a)] | 0.09[a)] | ≧3 |
| Nap | 5 | 0.2[a)] | 0.2[a)] | ≧3 |
| MNap | 3 | 0.18[a)] | 0.14[a)] | ≧2.5 |

[a)]Gel.
[b)]Suspension obtained after filtration through 0.45 μm filter

The solubility measurements indicate that all the lipid derivatives examined dissolve well in ethanol and octanol, i.e more than 10 mg/ml at room temperature. The resulted solutions are transparent and the compounds remain stable in the solution for at least several days at room temperature.

It is evident that the lipid derivatives according to the invention have acquired the desired hydrophobic properties that are advantageous for brain penetration and sequestration.

Example 7

In Vitro Cleavage of DP-DFC in Tissue Homogenates

The ability of the compounds of the invention to be cleaved to yield free diclofenac, was studied in vitro in homogenates of rat brain and liver. Two compounds were tested: the prodrug 1-Stearoyl-2-{4-[2-(2,6-dichloroanilino)-phenylacetamido]butanoyl}-sn-glycero-3-phosphocholine (DP-DFC; Z=3), and the compound 1-Stearoyl-2-{3-[2-(2,6-dichloroanilino)-phenylacetamido]propanoyl}-sn-glycero-3-phosphatidylcholine (DP-DFC; Z=2), comprising, respectively, a bridging group having a total of 4 and 3 carbon atoms.

Liver and brain were surgically removed, under pentobarbitone anesthesia, from male Sabra rats weighing 250–280 g. About 1–1.5 g samples from each tissue were homogenized in PBS pH=7.4 (Dulbecco) at a ratio of 1:9 w/v of tissue to buffer.

DP-DFC was added to each homogenate to a final concentration of 40 μg/ml. The mixtures were incubated at 37° C. in shaking for 1, 2, 3 and 6 hours, and then were placed on ice to stop the reaction.

The amounts of free diclofenac in 1 ml samples from either the brain or liver homogenates were determined by reverse phase HPLC assay. The amount of protein in each sample was assayed by the Lowry method.

The amounts of free diclofenac released at each time point, calculated per 1 mg of protein, are shown in Table 2. The result for each time point represents the average of five repetitions using tissues from five individual animals.

TABLE 2

In vitro cleavage of DP-DFC

| | Free DFC (μg/mg protein) | | | |
|---|---|---|---|---|
| | DP-DFC; Z = 3 | | DP-DFC; Z = 2 | |
| Time (hrs) | brain | liver | brain | liver |
| 0 | 0.05 | 0.07 | N.D | N.D |
| 1 | 0.36 ± 0.08 | 0.18 ± 0.09 | N.D | N.D |
| 2 | 0.65 ± 0.06 | 0.23 ± 0.05 | N.D | N.D |
| 3 | 0.75 ± 0.15 | 0.33 ± 0.14 | N.D | N.D |
| 6 | 1.30 ± 0.40 | 0.45 ± 0.14 | N.D | N.D |

N.D denotes undetectable amounts of free diclofenac.

As shown in Table 2, a significant cleavage of diclofenac from its lipid conjugate was demonstrated, both in the brain and liver homogenates, only for the prodrug DP-DFC; Z=3 and not for the compound DP-DFC; Z=2. These results assess the important role the bridging group plays in enabling the release of the drug from its phospholipid derivative.

Under the above-described experimental conditions, the amounts of diclofenac released from the prodrug in the brain and liver homogenates were equivalent, respectively, to 30% and 15% of the drug introduced as DP-DFC.

In order to evaluate the effect of temperature on the reaction, a parallel set of incubations was carried out at 4° C. It was found that cooling to 4° C. completely inhibited the cleavage of DP-DFC; Z=3 to DFC (data not shown).

The time and temperature dependent manner of the diclofenac release in the homogenates supports the conclusion that the drug is enzymatically cleaved from the prodrug molecule.

Example 8

In Vivo Sub-Chronic Toxicity Study of DP-DCF

DP-DCF compounds were evaluated for sub-chronic toxicity during 14-day drug administration period by following two criteria: a) monitoring body weight changes, and b) evaluating gastro-toxicity scores.

Male Sprague-Dawley rats weighing 250–280 g were kept under standard conditions for an acclimatization period of one week with food and water supplied ad lib. The rats were administered with commercial diclofenac (DCF; Sigma, USA) or with equivalent doses of 1-Stearoyl-2-{4-[2-(2,6-dichloroanilino)-phenylacetamido]butanoyl}-sn-glycero-3-phosphocholine (DP-DCF; Z=3) or 1-Stearoyl-2-{6-[2-(2,6-dichloroanilino)-phenylacetamido]hexanoyl}-sn-glycero-3-phosphocholine (DP-DCF; Z=5), p.o. by gavage daily for 14 days. Animals treated with the vehicle solution alone serve as control group.

The treatment groups were as follows:

| Group | No. of animals | Treatment | Dosage (mg/kg) |
|---|---|---|---|
| 1 | 5 | vehicle (control) | — |
| 2 | 5 | DCF | 10 |
| 3 | 5 | DP-DCF; Z = 3 | 30 |
| 4 | 5 | DP-DCF; Z = 5 | 30 |

A. Body Weight Changes

A major sign of general toxicity is decreasing of body weight. Male Sabra rats were treated as described above. The rats were weighed prior to dosing at the beginning of the experiment (day zero) and at the $5^{th}$, $9^{th}$ and $13^{th}$ day of the treatment. The percentage changes of body weight are shown in FIG. 1.

As can be seen in FIG. 1, DCF treated animals exhibit maximal decrease of body weight on day 5 of the experiment. In contrast to DCF treated animals, all the DP-DCF treated groups gained weight over 14 days with a similar profile to the vehicle treated group.

B. Toxicity Scores

Toxicity scores were assessed at the end of the 14-day multiple p.o drug administration period. On day 14, the animals were anesthetized 4 hours after administration of the test materials by i.p. injection of 0.5 ml pentobarbitone sodium (200 mg/ml) and laparatomy was preformed to remove the rat's stomach with approximately 15 mm of the associated duodenum. The stomachs were cut open along the small curvature and washed, with gentle rubbing, under running water. A semi-quantitative assessment of the gastric damage was determined by assigning scores ranging from 0 to 5. The scores indicate as follows: (0) No macroscopically visible lesions; (1) Hyperemia; (2) One-two slight lesions; (3) More than 2 slight lesions; (4) Severe lesions; (5) Perforation.

Figure 2:
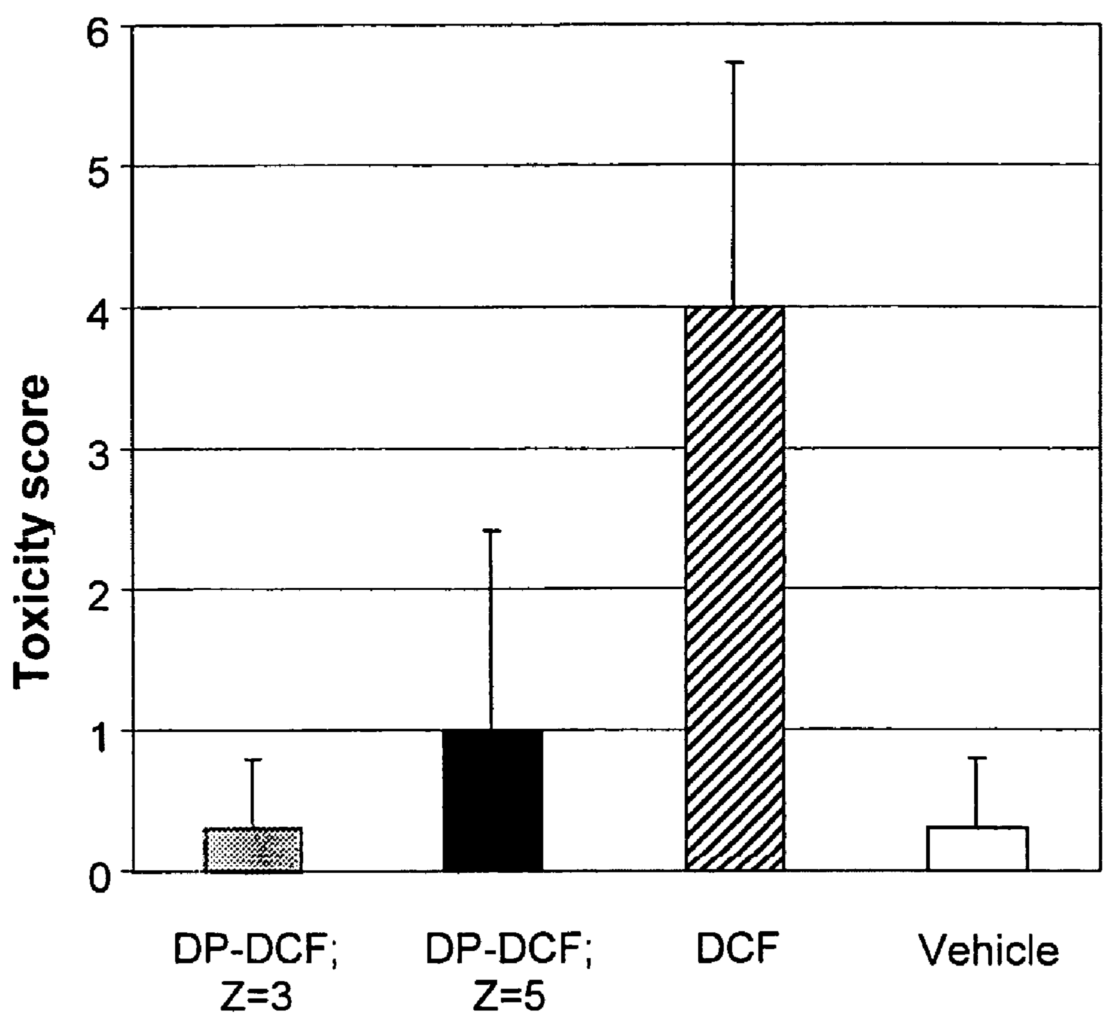
FIG. 2 depicts gastro-toxicity scores of rats after 14-day treatment with daily per os gavage of either vehicle (white bar), 10 mg/kg DCF (striped bar), 30 mg/kg DP-DCF; Z=3 (gray bar) or 30 mg/kg DP-DCF; Z=5 (black bar).

As shown in FIG. 2, the DP-DCF derivatives were less toxic than the parent drug, DCF. Both tested compounds, DP-DCF; Z=3 and DP-DCF; Z=5, show a better toxicological profile than diclofenac. The gastric side effects of DCF increase during multiple dosage administration and toxicity scores of 4 were reached by day 14. The irritant effects of the tested DP-DCF compounds were similar to that obtained with the vehicle, namely toxicity scores between 0.25 and 1.

Conclusion: As assessed by two parameters monitored during a 2-week study, the tested DP-DCFs were found to be substantially less toxic than the parent compounds. Normal weight gain was observed over two weeks in the DP-DCF treated animals compared with weight losses observed with the parent compound, diclofenac. The compounds of the invention were also shown to be less ulcerogenic as judged by the gastro-toxicity scores obtained after 14 days of chronic p.o. drug administration.

Example 9

In Vivo Penetration of Diclofenac into Rat Brain after i.v. Injection of DP-DFC

The time-dependent penetration of lipid conjugates of diclofenac is measured in rat serum and brain after i.v. administration of DP-DFC. 10 mg/kg of DP-DFC are intravenously injected to male Sabra rats weighing 250–280 g. The prodrug (5 mg/ml) is formulated as follows: 50 mg DP-DFC are dissolved in 300–400 μl ethanol, and Lipofundin® (B. Braun, Melsungen, Germany) is added upto a final volume of 10 ml. The amount of the formulated prodrug injected to the animals is 2 ml/kg body weight.

The animals are sacrificed either 0.5, 1, 2 or 3 hours following injection. Whole brain and blood samples are obtained from individual rats for each time point. The serum is separated by centrifugation of the blood (5 min. at about 800×g). The brain is treated as follows: whole brain is homogenized in saline. Half of the homogenate is extracted into organic solvents (methanol-chloroform 1:2) and is used for determination the level of the lipid derivative (DP-DFC). The other half is acidified by 85% $H_3PO_4$, extracted into chloroform and is used for determination of the level of free diclofenac (DFC). Each of the organic phases is separated by centrifugation, dried over $Na_2SO_4$ and evaporated. The obtained residues are dissolved in the corresponding mobile phase used in the HPLC method, and the amounts of both DP-DFC and DFC are determined by reverse phase HPLC.

Conclusion: Following i.v. administration of the prodrug, DP-DFC penetrates the blood-brain barrier (BBB).

Example 10

Anti-Inflammatory Activity of DP-DFC (In Vivo Efficacy Study)

Efficacy of DP-DFC lipid derivatives was tested in vivo in the model system of rodent carrageenan edema test.

Carrageenan-induced rat paw edema is a widely employed animal model for acute inflammation. The objective of the study is to assess the potential prophylactic effects of DP-DCF derivatives on the prevention of inflammatory swelling and, in particular, to compare the efficacy parameters with those obtained for diclofenac. The experimental set-up was as follows: Male Sprague-Dawley rats weighing 120–180 g (supplied by Harlan Laboratories Breeding Center, Israel) were intraperitoneally (i.p.) injected with drug or prodrug one hour prior to the induction of inflammation with carrageenan. Animals injected with vehicle alone served as control group.

Paw edema was induced by a single sub-plantar injection of 0.1 ml 2% carrageenan in physiological saline, into test animals' right hind paws. Just prior to paw edema induction, the paw thickness of the test animals' right hind paws was measured in triplicate using a plethysmograph and micrometer to provide a baseline. At 3, 5 and 7 hours post carrageenan injection, the right paw thickness was measured in the same manner as before.

Potential anti-inflammatory activity in suppressing carrageenan-induced paw oedema was assessed by the relative differences in paw volumes between pre- and post-carrageenan measurements, expressed as (%) change.

Dose levels were 10 mg/kg i.p. for diclofenac and 30 mg/kg (dose equivalent) for the DP-DCF derivatives. 10 ml/kg of the carrier solution was used for the vehicle control.

Figure 3:
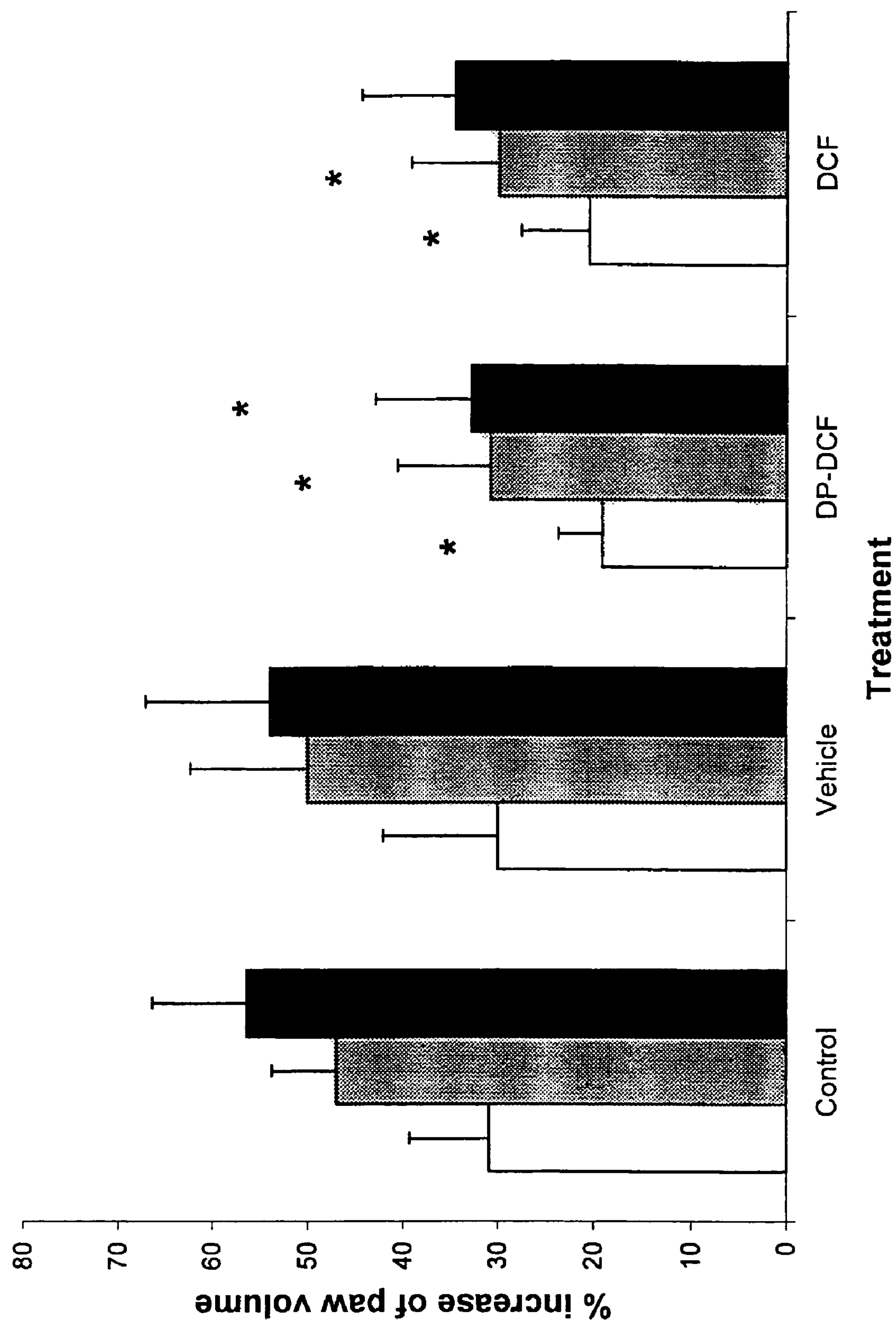
FIG. 3 depicts effects of DCF (10 mg/kg) and DP-DCF; Z=5 (30 mg/kg) on Carrageenan-induced paw oedema in rats. The treated animals' paw volumes were measured at 3, 5 and 7 hours post-Carrageenan injection (white, gray and black bars, respectively) and are presented as percentage increase of paw volume. Statistically significant effects ($p<0.05$) are indicated by asterisks (*).

In FIG. 3 are presented the results obtained with one of the DP-derivatives, DP-DCF; Z=5, in comparison to those obtained with the parent compound, diclofenac. As can be seen in FIG. 3, both DCF and the DP-DCF derivative demonstrated statistically significant and consistent anti-inflammatory activity throughout the 7-hour post-carrageenan measurement period (level of significance is $p<0.05$ by statistical analysis using the Student's t-test). Anti-inflammatory activity was already found at the 3-hour post-carrageenan measurement.

Example 11

Neuroprotective Effects of DP-DCF

Neuroprotective effects of compounds of the invention were examined in the global forebrain ischemic model system in Mongolian gerbils.

Male Mongolian gerbils 60–70 g (Charles River Laboratories, USA) were used in this study. Global forebrain ischemia was induced by transient occlusion of both carotid arteries for 10 minutes, using arterial clips. The tested compounds were orally administered to the animals, 7–8 animals per group, by either one of two schemes:

a) single dose administration of commercial diclofenac (Sigma, USA; 10 mg/kg) or dose-equivalent of DP-DCF; Z=5 (30 mg/kg). The administration was per os (p.o.) two hours before induction of ischemia (FIG. 4);
b) multiple dosing of DP-DCF; Z=5 (30 mg/kg) orally administered daily for 5 days beginning four days prior to induction of ischemia. (FIG. 5).

In both schemes, animals treated with vehicle alone served as control groups. Blood samples were withdrawn from eye sinuses of the animals 24 hours after the onset of ischemia and serum levels of neuron specific enolase (NSE) were determined by radioimmunoassay using NSE kit (Pharmatope Ltd., Israel). The measured NSE levels, expressed in ng/ml, are summarized in FIGS. 4 and 5.

It has been shown that serum levels of NSE are elevated in the event of ischemic insult. Thus, serum level of NSE may serve as a marker for the degree of neuronal damage (Barone et al. (1993) Brain Res. 623: 77–82).

Figure 4:
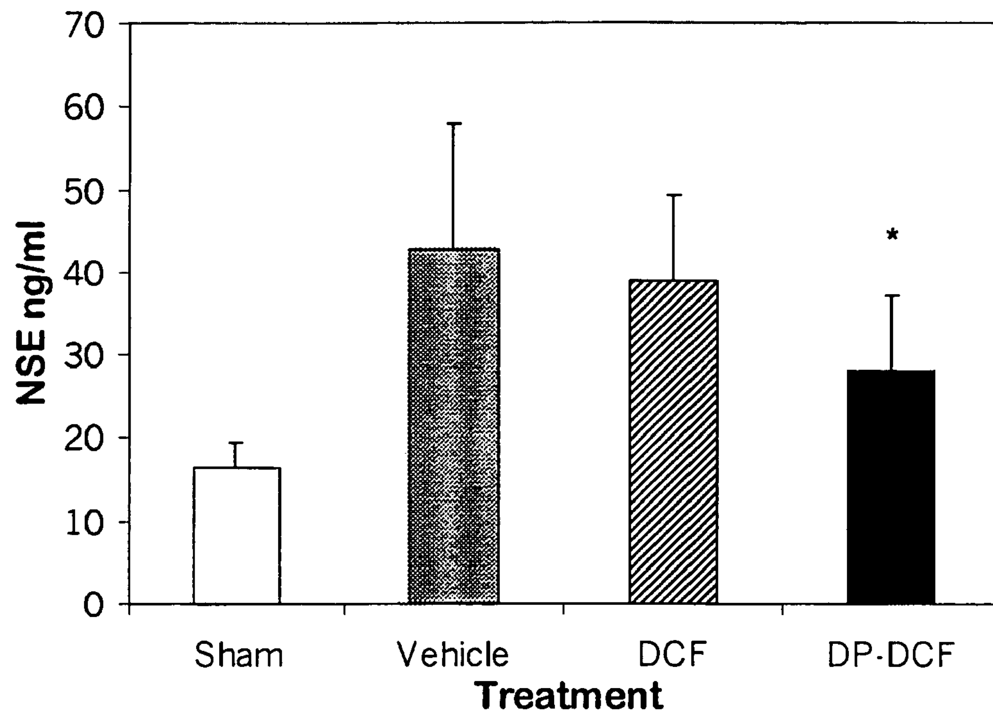
FIG. 4 depicts levels of neuron specific enolase (NSE) measured in the serum of Mongolian gerbils 24 hours following induction of global forebrain ischemia. The gerbils were treated by single oral administration of 10 mg/kg DCF (striped bar), 30 mg/kg DP-DCF; Z=5 (black bar) or vehicle (gray bar) two hours prior to induction of ischemia. NSE level in sham operated animals is presented by a white bar. Statistically significant effect ($p<0.05$) is indicated by an asterisk (*).
Figure 5:
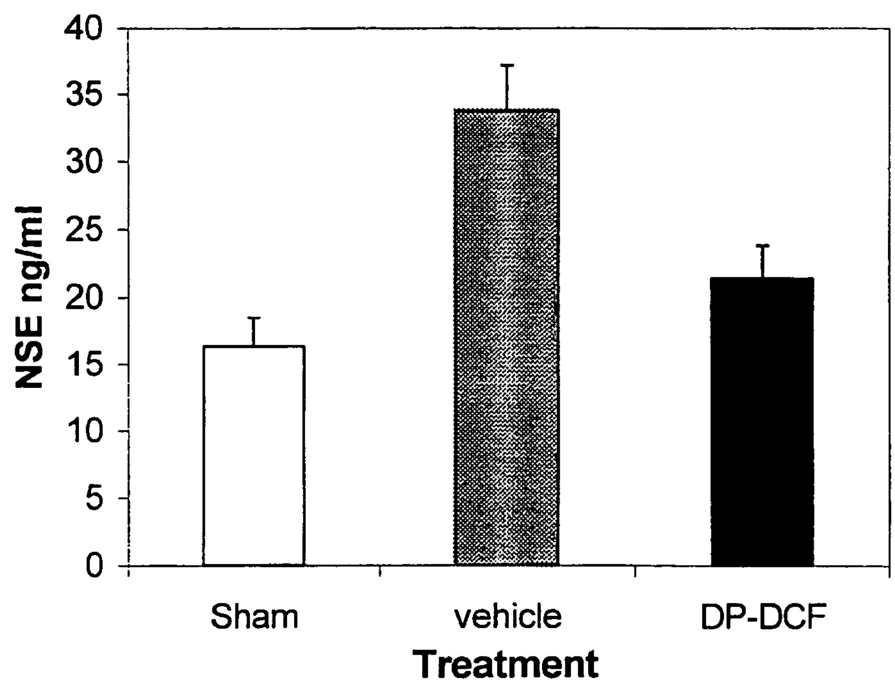
FIG. 5 depicts levels of neuron specific enolase (NSE) measured in the serum of Mongolian gerbils 24 hours following induction of global forebrain ischemia. The gerbils were treated by daily oral administration of 30 mg/kg DP-DCF; Z=5 (black bar) or vehicle (gray bar) for 5 days, beginning 4 days prior to induction of ischemia. NSE level in sham operated animals is presented by a white bar.

As shown in FIG. 4, NSE level in serum of animals treated with single dose of DP-DCF is reduced in comparison to NSE level in serum of animals that were treated with DCF or vehicle alone. The parent drug, diclofenac, penetrates the brain poorly and is not expected to have an effect on NSE level changes associated with brain ischemia.

As shown in FIG. 5, which summarizes the results of the multiple dosing experiment, also in this case there is significant reduction in NSE level found in the serum of animals treated with the DP-DCF compound ($p<0.05$).

Conclusion: The tested DP-DCF derivative exhibits neuronal protective effect, as indicated by the significant reduction in NSE activity in the serum, measured after global cerebral ischemia. The effect was demonstrated in both single and multiple dosing schemes.

While the present invention has been particularly described, persons skilled in the art will appreciate that many variations and modifications can be made. Therefore, the invention is not to be construed as restricted to the particularly described embodiments, rather the scope, spirit and concept of the invention will be more readily understood by reference to the claims which follow.

The invention claimed is:

1. A compound of the general formula I

Formula I

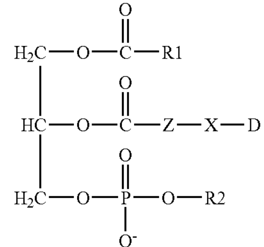

or a pharmaceutically acceptable salt thereof, wherein:

R1 is a saturated or unsaturated hydrocarbon chain having from 2 to 30 carbon atoms;

R2 is a phospholipid head group;

D is a residue of ibuprofen, wherein D is attached through a functional group to a bridging group, —C(O)-Z-X—, wherein Z is a saturated or unsaturated hydrocarbon chain having from 2 to 15 carbon atoms, and X is an amino group.

2. The compound according to claim 1, wherein the conjugated residue of ibuprofen is pharmacologically inactive.

3. The compound according to claim 1, wherein an ester bond at position sn-2 of the phospholipid of the general formula I is cleaveable by a lipase.

4. The compound according to claim 3, wherein said lipase is a phospholipase.

5. The compound according to claim 4, wherein said phospholipase is phospholipase $A_2$ ($PLA_2$).

6. The compound according to claim 1, wherein R1 is an hydrocarbon chain having from 10 to 20 carbon atoms.

7. The compound according to claim 1, wherein R1 is an hydrocarbon chain having 15 or 17 carbon atoms.

8. The compound according to claim 1, wherein R2 is selected from the group consisting of choline, ethanolamine, inositol and seine.

9. The compound according to claim 1 selected from the group consisting of:

1-Stearoyl-2-{3-[α-methyl-4-(2-methylpropyl)benzene-acetamido]propanoyl}-sn-glycero-3-phosphocholine, and 1-Stearoyl-2-{6-[α-methyl-4-(2-methylpropyl)benzene-acetamido]hexanoyl}-sn-glycero-3-phosphocholine.

10. A pharmaceutical composition comprising a pharmaceutically acceptable carrier and, as an active ingredient, a compound of the general formula I Formula I

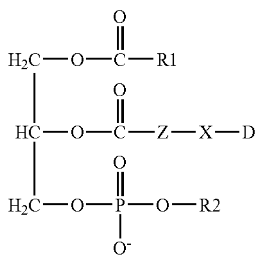

or a pharmaceutically acceptable salt thereof, wherein:

R1 is a saturated or unsaturated hydrocarbon chain having from 2 to 30 carbon atoms;

R2 is a phospholipid head group;

D is a residue of ibuprofen, wherein D is attached through a functional group to a bridging group, —C(O)-Z-X—, wherein Z is a saturated or unsaturated hydrocarbon chain having from 3 to 15 carbon atoms, and X is an amino group.

11. The pharmaceutical composition according to claim 10, wherein —C(O)-Z-X-D is an inactive derivative of ibuprofen.

12. The pharmaceutical composition according to claim 10, wherein an ester bond at position sn-2 of the phospholipid of the general formula I is cleaveable by a lipase.

13. The pharmaceutical composition according to claim 12, wherein said lipase is a phospholipase.

14. The pharmaceutical composition according to claim 13, wherein said phospholipase is phospholipase $A_2$ ($PLA_2$).

15. The pharmaceutical composition according to claim 10, wherein R1 is an hydrocarbon chain having from 10 to 20 carbon atoms.

16. The pharmaceutical composition according to claim 10, wherein R1 is an hydro carbon chain having 15 or 17 carbon atoms.

17. The pharmaceutical composition according to claim 10, wherein R2 is selected from the group consisting of choline, ethanolamine, inositol and serine.

18. The pharmaceutical composition according to claim 10, wherein said compound of the general formula I is selected from the group consisting of:

1-Stearoyl-2-{3-[α-methyl-4-(2-methylpropyl)benzene-acetamido]propanoyl}-sn-glycero-3-phosphocholine, and 1-Stearoyl-2-{6-[α-methyl-4-(2-methylpropyl)benzene-acetamido]hexanoyl}-sn-glycero-3-phosphocholine.

19. The pharmaceutical composition according to claim 10, in the form of solutions, suspensions, capsules, tablets, aerosols, gels, ointments or suppositories.

20. The pharmaceutical composition according to claim 10 for oral, ocular, nasal, parenteral, topical or rectal administration.

21. The pharmaceutical composition according to claim 20 for oral administration.

22. The pharmaceutical composition according to claim 20 for nasal administration.

23. The pharmaceutical composition according to claim 10 for the treatment of a disease or disorder related to an inflammatory condition selected from the group consisting of arthritis, rheumatoid arthritis, asthma, psoriasis, systemic lupus erythematosus, inflammatory bowel syndrome, multiple sclerosis, Alzheimer's disease, Parkinson's disease, Huntington's disease, vascular dementia, epilepsy, migraines, stroke and trauma.

24. A method for treatment of inflammation comprising administering to a patient in need thereof a therapeutically effective amount of a pharmaceutical composition according to claim 10.

25. The method for treatment of a disease or disorder related to an inflammatory condition comprising administering to a patient in need thereof a therapeutically effective amount of a pharmaceutical composition according to claim 10, wherein said disease or disorder related to an inflammatory condition is selected from the group consisting of arthritis, rheumatoid arthritis, asthma, psoriasis, systemic lupus erythematosus, inflammatory bowel syndrome, multiple sclerosis, Alzheimer's disease, Parkinson's disease, Huntington's disease, vascular dementia, epilepsy, migraines, stroke and trauma.

26. A process for the synthesis of compounds of the general formula I as defined in claim 1, comprising:

(i) providing a molecule y-X-Z-COOH, wherein y is selected from H and OH, Z is a saturated or unsaturated hydrocarbon chain having from 2 to 15 carbon atoms, and X is an amino group;

(ii) replacing y with an appropriate blocking group, B, selected from the group consisting of benzyl chloromate, benzyloxycarbonate, diphenylcarbinol and trimethylacetamidocarbinol;

(iii) preparing an anhydride of the molecule B—X-Z-COOH by employing a reagent to remove one molecule of water from two protected bridging groups;

(iv) acylating a lyso-lecithin by the anhydride of step (iii) to yield 1-acyl-2-acyl(X—B)-sn-glycero-3 phospholipid by dissolving said anhydride and said lyso-lecithin in an organic solvent in the presence of a catalyst;

(v) removing the blocking group B from the functional group X; and (vi) coupling a nonsteroidal anti-inflammatory drug D comprising ibuprofen to the functional group X in an organic solvent in the presence of reagents that enable a condensation reaction wherein water molecules are removed, thus, generating a molecule of the general Formula I.

27. The process according to claim 26 wherein the protected functional group X is —NH.

28. The process according to claim 26 wherein the phospholipid of step (iv) is phosphatidyleholine, phosphatidylethanolamine, phosphatidylinositol or phosphatidylserine.

29. The compound according to claim 1, wherein R1 is a saturated hydrocarbon chain having from 10 to 20 carbon atoms.

30. The pharmaceutical composition according to claim 10, wherein R1 is a saturated hydrocarbon chain having from 10 to 20 carbon atoms.

* * * * *